United States Patent [19]
Hallinan et al.

[11] Patent Number: 6,143,790
[45] Date of Patent: *Nov. 7, 2000

[54] L-N⁶-(1-IMINOETHYL)LYSINE DERIVATIVES USEFUL AS NITRIC OXIDE SYNTHASE INHIBITORS

[75] Inventors: E. Ann Hallinan, Evanston, Ill.; Foe S. Tjoeng, Manchester; Kam F. Fok, St. Louis, both of Mo.; Timothy J. Hagen, Gurnee, Ill.; Mihaly V. Toth, St. Louis, Mo.; Sofya Tsymbalov, Des Plaines; Barnett S. Pitzele, Skokie, both of Ill.

[73] Assignee: G.D. Searle & Co., Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/702,695

[22] PCT Filed: Mar. 8, 1995

[86] PCT No.: PCT/US95/02669

§ 371 Date: Sep. 6, 1996

§ 102(e) Date: Sep. 6, 1996

[87] PCT Pub. No.: WO95/24382

PCT Pub. Date: Sep. 14, 1995

Related U.S. Application Data

[63] Continuation-in-part of application No. 08/209,094, Mar. 10, 1994, abandoned.

[51] Int. Cl.⁷ ........................ A61K 31/155; A61K 31/42; A61K 31/38; A61K 31/22
[52] U.S. Cl. .......................... 514/631; 514/374; 514/381; 514/400; 514/438; 514/448; 514/452; 514/467; 514/471; 514/546; 514/547; 514/634; 514/637; 514/825; 514/866; 514/921; 548/235; 548/254; 548/236.5; 549/72; 549/75; 549/274; 549/229; 549/451; 549/495; 560/251; 564/225; 564/240; 564/246
[58] Field of Search .................................. 514/631, 825, 514/866, 920, 634, 374, 381, 400, 438, 448, 452, 467, 471, 546, 547, 637, 921; 564/225, 240, 246; 560/251; 549/72, 75, 278, 229, 451, 495; 548/235, 254, 336.5

[56] References Cited

U.S. PATENT DOCUMENTS

| | | | |
|---|---|---|---|
| 3,201,459 | 8/1965 | Coda et al. | 564/240 |
| 3,202,710 | 8/1965 | Bolger | 564/240 |
| 4,713,369 | 12/1987 | Stüber | 514/18 |
| 5,059,624 | 10/1991 | Monache et al. | 564/240 |
| 5,059,712 | 10/1991 | Griffith | 562/560 |
| 5,081,148 | 1/1992 | Braquet et al. | 514/162 |
| 5,132,453 | 7/1992 | Griffith | 562/560 |
| 5,196,450 | 3/1993 | Sjoerdsma et al. | 514/565 |
| 5,273,875 | 12/1993 | Griffith | 435/1 |
| 5,281,627 | 1/1994 | Griffith | 514/565 |
| 5,362,744 | 11/1994 | Purchase, Jr. et al. | 514/381 |
| 5,364,881 | 11/1994 | Griffith et al. | 514/508 |
| 5,416,238 | 5/1995 | Abe et al. | 564/240 |
| 5,464,858 | 11/1995 | Griffith et al. | 514/399 |

FOREIGN PATENT DOCUMENTS

| | | |
|---|---|---|
| 0370320 | 5/1990 | European Pat. Off. . |
| 0446699 | 9/1991 | European Pat. Off. . |
| 2240041 | 7/1991 | United Kingdom . |
| 91/04023 | 4/1991 | WIPO . |
| 91/04024 | 4/1991 | WIPO . |
| 93/13055 | 7/1993 | WIPO . |
| 93/16721 | 9/1993 | WIPO . |
| 93/24126 | 12/1993 | WIPO . |
| 94/14780 | 7/1994 | WIPO . |
| 95/00505 | 1/1995 | WIPO . |
| 95/11014 | 4/1995 | WIPO . |
| 96/06076 | 2/1996 | WIPO . |

OTHER PUBLICATIONS

Gould et al., "Nucleoside Intermediates in Blasticidin S Biosynthesis Identified by the In Vivo Use of Enzyme Inhibitors", *Can. J. Chem.*, vol. 72, pp. 6–11, 1994.

Tsunematsu et al., "β–Naphthylamides of Guanidinophenyl Amino Acids as Substrates of Aminopeptidases", *Chem. Pharm. Bull.*, vol. 36, No. 3, pp. 1205–1209, 1988.

Funabashi et al., "A New Anti–MRSA Dipeptide, TAN–1057 A", *Tetrahedron*, vol. 49, No. 1, pp. 13–28, 1993.

Prabhakaran et al., "Studies on Nitrogen Metabolism Using ¹³C NMR Spectroscopy. 5.¹ Metabolism of L–α–Arginine in the Biosynthesis of Blasticidin S", *Tetrahedron*, vol. 27, No. 33, pp. 3815–3818, 1986.

Stuehr et al., "Mammalian Nitric Oxide Synthases", *Advances in Enzymology*, vol. 65, 1992, (p. 317).

Plapp et al., "Determintion of ε–Acetimidyllysine in Proteins" *Analytical Biochemistry*, vol. 62, pp. 291–294, 1974.

Rees et al., "Characterization of Three Inhibitors of Endothelial Nitric Oxide Synthase in vitro and in vivo", *Br. J. Pharmacol.*, vol. 101, pp. 746–752, 1990.

Proudfoot et al., "Conformation–directed Recombination of Enzyme–activated Peptide Fragments: A Simple and Efficient Means to Protein Engineering", *J. Bio. Chem.*, vol. 264, No. 15, pp. 8764–8770, 1989.

Palacios, et al., "Nitric Oxide from L–Arginine Stimulates the Soluble Guanylate Cyclase in Adrenal Glands", *Biochemical and Biophysical Research Communications*, vol. 165, No. 2, pp. 802–809, 1989.

Knowles et al., "Kinetic Characteristics of Nitric Oxide Synthase from Rat Brain", *Biochem. J.*, vol. 269, pp. 207–210, 1990.

CA 107, 40336y, 1987.
CA 63, 5641d, 1965.
CA 97, 38442m, 1982.
CA 76, 43768t, 1972.
CA 118, 72838g, 1993.
CA 64, 17593h, 1966.
CA 115, 29868t, 1991.
CA 104, 202858, 1986.

*Primary Examiner*—Peter O'Sullivan
*Attorney, Agent, or Firm*—Alan L. Scrivner

[57] ABSTRACT

There is disclosed a novel amino glycol derivatives of L-N⁶-(1-iminoethyl)lysine, pharmaceutical compositions containing these novel compounds, and to their use in therapy, in particular their use as nitric oxide synthase inhibitors.

28 Claims, No Drawings

L-N⁶-(1-IMINOETHYL)LYSINE DERIVATIVES USEFUL AS NITRIC OXIDE SYNTHASE INHIBITORS

RELATED APPLICATION

This application is a 371 of PCT/US95/02669 filed Mar. 8, 1995 which is a continuation-in-part of U.S. application Ser. No. 08/209,094 filed Mar. 10, 1994 now abandoned.

BACKGROUND OF THE INVENTION

1. Field of the Invention

The present invention relates to novel amino glycol derivatives of L-N⁶-(1-iminoethyl)lysine, pharmaceutical compositions containing these novel compounds, and to their use in therapy, in particular their use as nitric oxide synthase inhibitors.

2. Related Art

It has been known since the early 1980's that the vascular relaxation brought about by acetycholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite, glyceryltrinitrite and other nitrovasodilators. The recent identification of EDRF as NO has coincided with the discovery of a biochemical pathway by which NO is synthesized from the amino acid L-arginine by the enzyme NO synthase.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al, *Biochemical Pharmacology*, 38, 1709–1715 (1989) and Moncada et al, *Pharmacological Reviews*, 43, 109–142 (1991).

It is now thought that excess NO production may be involved in a number of conditions, particularly conditions which involve systemic hypotension such as toxic shock and therapy with certain cytokines.

The synthesis of NO from L-arginine can be inhibited by the L-arginine analogue, L-N-monomethyl-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least three types of NO synthase as follows:

(i) a constitutive, Ca⁺⁺/calmodulin dependent enzyme, located in the endothelium, that releases NO in response to receptor or physical stimulation.

(ii) a constitutive, Ca⁺⁺/calmodulin dependent enzyme, located in the brain, that releases NO in response to receptor or physical stimulation.

(iii) a Ca⁺⁺ independent enzyme which is induced after activation of vascular smooth muscle, macrophages, endothelial cells, and a number of other cells by endotoxin and cytokines. Once expressed this inducible NO synthase synthesizes NO for long periods.

The NO released by the constitutive enzymes acts as a transduction mechanism underlying several physiological responses. The NO produced by the inducible enzyme is a cytotoxic molecule for tumor cells and invading microorganisms. It also appears that the adverse effects of excess NO production, in particular pathological vasodilation and tissue damage, may result largely from the effects of NO synthesized by the inducible NO synthase.

There is also a growing body of evidence that NO may be involved in the degeneration of cartilage which takes place in certain conditions such as arthritis and it is also known that NO synthesis is increased in rheumatoid arthritis. Accordingly, further conditions in which there is an advantage in inhibiting NO production from L-arginine include autoimmune and/or inflammatory conditions affecting the joints, for example arthritis, inflammatory bowel disease, cardiovascular ischemia, diabetes, hyperalgesia (allodynia), cerebral ischemia (both focal ischemia, thrombotic stroke and global ischemia, secondary to cardiac arrest), and other CNS disorders mediated by NO.

Futher conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy.

Some of the NO synthase inhibitors proposed for therapeutic use so far, and in particular L-NMMA, are non-selective in that they inhibit both the constitutive and the inducible NO synthase. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use.

WO94/12165, WO94/14780, WO93/13055, EP0446699A1 and U.S. Pat. No. 5,132,453 disclose compounds that inhibit nitric oxide synthesis and preferentially inhibit the inducible isoform of nitric oxide synthase. The disclosures of which are hereby incorporated by reference in their entirety as if written herein.

SUMMARY OF THE INVENTION

In accordance with the present invention novel amino glycol derivatives of L-N⁶-(1-iminoethyl)lysine derivatives are provided. These novel inhibitor compounds can be represented by the following chemical formula. A compound or a pharmaceutically acceptable salt, prodrug or ester therof having the formula:

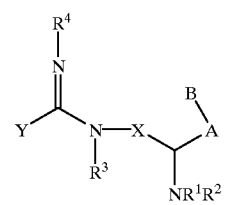

Y is a hydrogen, lower alkyl radical, lower alkenyl radical, lower alkynyl radical, aromatic hydrocarbon radical, alicyclic hydrocarbon radical, amino, heterocyclyl radical in which 1 to about 4 heteroatoms are independently selected from oxygen, nitrogen and sulfur, wherein all said radicals may optionally be substituted with hydrogen, cyano, lower alkyl, nitro, amino, alicyclic hydrocarbon radicals, or aromatic hydrocarbon radicals which may be optionally substituted with lower alkyl;

X is lower alkyl radical, lower alkenyl radical, lower alkynyl radical, aromatic hydrocarbon radical, $(CH_2)_m Q(CH_2)_n$, where m=1–3, n=1–3, and Q is sulfur, sulfinyl, sulfonyl or oxygen, C=O, lower alkynyl radical, aromatic hydrocarbon radical, alicyclic hydrocarbon radical or heterocyclyl radicals in which 1 to about 4 heteroatoms are independently selected from oxygen, nitrogen and sulfur, wherein all said radicals are optionally substituted with hydrogen, halogen and lower alkyl;

$R^1$, $R^2$, $R^3$ and $R^4$ are independently selected from the group consisting of hydrogen and lower alkyl;

A is a lower alkyl radical, lower alkenyl radical, lower alkynyl radical, alicyclic hydrocarbon radical, C=O, aromatic hydrocarbon radical or heterocyclyl radical in which 1 to about 4 heteroatoms are independently selected from oxygen, nitrogen and sulfur, wherein all said radicals are optionally substituted with hydrogen, lower alkyl, hydroxyl, lower alkoxy, alkoxycarbonyl, alkylaryloxy, thiol, lower thioalkoxy, thioalkylaryloxy, thioaryloxy, sulfinylalkyl, sulfinylalkylaryl, sulfinylaryl, sulfonylalkyl, sulfonylalkylaryl, sulfonylaryl, halogen, aromatic hydrocarbon radicals, or alicyclic hydrocarbon radicals;

B can be hydrogen, lower alkyl radical, lower alkenyl radical, lower alkynyl radical, lower alkoxy radical, hydroxy, alkoxycarbonyl, alkylaryloxy, thiol, lower thioalkoxy, lower thioalkylaryloxy, thioaryloxy, sulfinylalkyl, sulfinylalkylaryl, sulfinylaryl, sulfonylalkyl, sulfonylalkylaryl, sulfonylaryl, aromatic hydrocarbon radical, alicyclic hydrocarbon radical, or heterocyclyl radical in which 1 to about 4 heteroatoms are independently selected from oxygen, nitrogen and sulfur wherein all said radicals are optionally substituted with hydrogen, lower alkyl, hydroxyl, lower alkoxy, halogen, aromatic hydrocarbon radicals, or alicyclic hydrocarbon radical, or B can be $C(=O)OR^5$, $C(=O)NR^5R^6$, $P(=O)(OR^5)(OR^6)$, NHOH, $N(OH)C(=O)NR^5R^6$, $NR^5C(=O)NR^6R^7$, $NR^5C(=CO)N(OH)R^6$, $C(=O)NHOH$, where $R^5$ is hydrogen, lower alkyl radical, aromatic hydrocarbon radical, or alicyclic hydrocarbon radical wherein all said radicals are optional substituted with lower alkyl, lower alkenyl;

$R^6$ is hydrogen, lower alkyl radical, aromatic hydrocarbon radical, or alicyclic hydrocarbon radical wherein all said radicals are optional substituted with lower alkyl, lower alkenyl; and $R^7$ is hydrogen, lower alkyl radical, aromatic hydrocarbon radical, or alicyclic hydrocarbon radical wherein all said radicals are optional substituted with lower alkyl, lower alkenyl;

with the proviso that when A is C=O, B may not be hydroxy or alkoxy.

A is preferably lower alkyl which is substituted as indicated above.

In another broad aspect, the present invention is directed to inhibiting nitric oxide synthesis in a subject in need of such inhibition or treatment by administering a compound of Formula (I) which preferentially inhibits the inducible isoform of nitric oxide synthase over the constitutive isoform of nitric oxide synthase, in a nitric oxide synthesis inhibiting amount to such subject.

The invention further relates to a pharmaceutical composition comprising a compound from Formula (I).

Compounds and compositions defined above have usefulness as inhibitors of nitric oxide synthase. These compounds also preferentially inhibit the inducible form over the constitutive form by at least 3 fold.

Conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy. Further conditions in which there is an advantage in inhibiting NO production from L-arginine include autoimmune diseases and/or inflammatory conditions such as those affecting the joints, for example arthritis or inflammatory bowel disease, cardiovascular ischemia, diabetes, cerebral ischemia and other CNS disorders mediated by NO.

A preferred embodiment of the present invention is a compound of the formula (I) wherein Y is hydrogen or lower alkylene X is lower alkylene from 3–5 carbon $R^1$, $R^2$, $R^3$, and $R^4$ are independently selected from the group consisting of hydrogen or lower alkyl A is lower alkylene from 2–4 carbons sustituted with hydroxyl B is hydroxyl.

It is preferred that Y is methyl, X is preferably butylene, $R^1$, $R^2$, $R^3$, and $R^4$ are preferably hydrogen, A is preferably ethylene or isopropylene substituted with hydroxyl and B is preferably hydroxyl (OH).

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulfuric, citric, tartaric, phosphoric, lactic, acetic, succinic, fumaric, maleic, methanesulfonic, ethanesulfonic, p-toluenesulfonic, benzenesulfonic and the like. (See, for example, S. M. Berge et al., Pharmaceutical Salts, *J. Pharm. Sci.*, 1977, 66, 1–19.) Salts of the compounds of formula (I) can be made by reacting the appropriate compound in the form of the free base with the appropriate acid.

While it may be possible for the compounds of formula (I) to be administered as the raw chemical, it is preferable to present them as a pharmaceutical formulation. According to a further aspect, the present invention provides a pharmaceutical formulation comprising a compound of formula (I) or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, pentenylen-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alicyclic hydrocarbon" or "cycloalkyl" means a aliphatic radical in a ring with 3 to about 10 carbon atoms, and preferably from 3 to about 6 carbon atoms. Examples of suitable alicyclic radicals include cyclopropyl, cyclobutyl, cyclopentyl, cyclohexyl, cyclohexenyl and the like.

The term "aromatic hydrocarbon radical" means 4 to about 16 carbon atoms, preferably 6 to about 12 carbon atoms, more preferably 6 to about 10 carbon atoms. Examples of suitable aromatic hydrocarbon radicals include phenyl, naphthyl, and the like.

The term "aryl" as used herein means 5- and 6-membered single-aromatic radicals which may include from zero to four heteroatoms. Representative aryls include phenyl, thienyl, furanyl, pyridinyl, (is)oxazoyl and the like.

The term DCM means dichloromethane.
The term DEAD means diethyl azodicarboxylate.
The term DIBAL-H means diisobutylaluminum hydride.
The term DMAP means dimethylaminopyridine.
The term DMSO means dimethylsulfoxide.
The term EDC means 1-(3-dimethylaminopropyl)-3-ethylcarbodiimide hydrochloride.

The term "heterocyclyl radical" means a saturated or unsaturated cyclic hydrocarbon radical including aromatic systems with 4 to about 10 carbon atoms, preferably about 5 to about 6; wherein 1 to about 4 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, isoxazolyl, thiazolyl, imidazolyl, indolyl, thienyl, furanyl, tetrazolyl, 2-pyrrolinyl, 3-pyrrolinyl, pyrrolindinyl, 1,3-dioxolanyl, 2-imidazonlinyl, imidazolidinyl, 2-pyrazolinyl, pyrazolidinyl, isoxazolyl, isothiazolyl, oxadiazolyl, triazolyl, thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, triazinyl, 1,3,5-trithianyl, benzo(b)thiophenyl, benzimidazolyl, quinolinyl, and the like.

The term HOBT means N-hydroxybenzotriazole.

The term "lower alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, iso-butoxy, sec-butoxy, tert-butoxy and the like.

The term "lower thioalkoxy", alone or in combination, means an alkyl thioether radical wherein the term alkyl is as defined above and most preferably containing 1 to about 4 carbon atoms. Examples of suitable alkyl thioether radicals include thiomethoxy, thioethoxy, thio-n-propoxy, thio-i-propoxy, thio-n-butoxy, thio-iso-butoxy, thio-sec-butoxy, thio-tert-butoxy and the like.

The term alkoxycarbonyl as used herein means an alkoxy group, as defined above, having a carbonyl (C=O) group attached.

The term "halogen" means fluorine, chlorine, bromine or iodine.

The term mcpba means m-chloroperbenzoic acid.

The term NMM means N-methylmorpholine.

The term NMMO means 4-methylmorpholine N-oxide.

The term "prodrug" refers to a compound that is made more active in vivo.

The term sulfinyl means SO.

The term sulfonyl means $SO_2$.

The term TEA means triethylamine.

The term $TMSN_3$ means azidotrimethylsilane.

As used herein, reference to "treatment" of a patient is intended to include prophylaxis.

All references, patents or applications, U.S. or foreign, cited in the application are hereby incorporated by reference as if written herein.

Compounds of the present invention can exist in geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention.

Disclosed are twenty eight general synthetic processes useful in the preparation of the compounds of the present invention.

Scheme 1

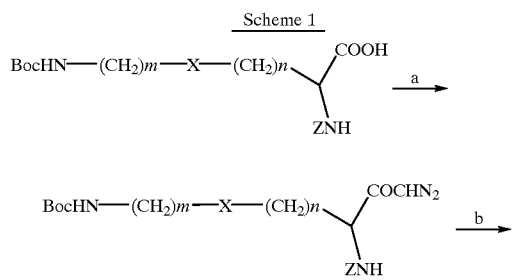

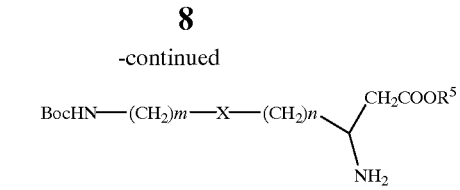

(a) (i) i-butyl chloroformate, NMM, THF; (ii) $CH_2N_2$; (b) Ag benzoate, $R^5OH$, TEA.

Scheme 2

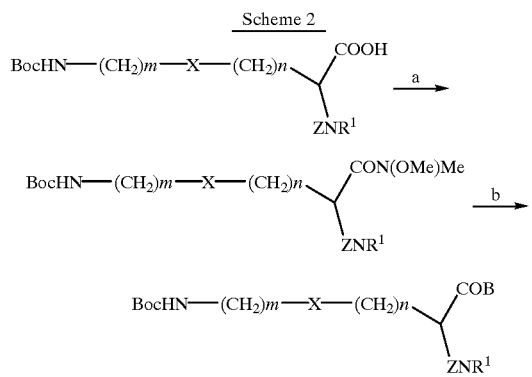

(a) N,O-Dimethylhydroxylamine HCl, EDC, HOBT, TEA, DMF; (b) B*Li, THF.
*see generic claims for B = alkyl, aryl, heteroaryl Scheme 3

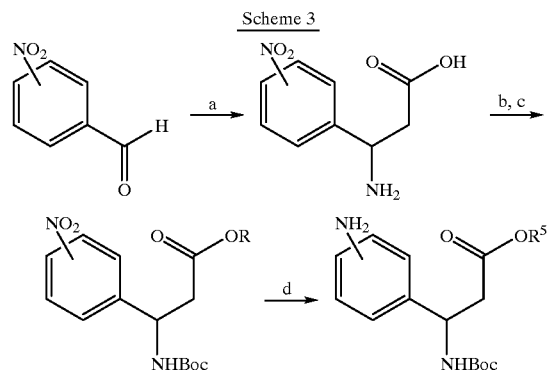

(a) ammonium acetate, malonic acid, acetic acid; (b) di-t-butyl dicarbonate, NaOH/dioxane; (c) $NaHCO_3$, DMF, $R^5I$; (d) $H_2$ Pd/C.

Scheme 4

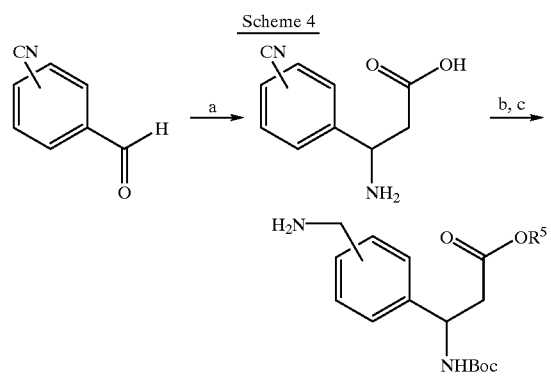

(a) ammonium acetate, malonic acid, acetic acid; (b) di-t-butyl dicarbonate, NaOH/dioxane; (c) $NaHCO_3$, DMF, $R^5I$; (d) $H_2$ Pd/C.

6,143,790

Scheme 5

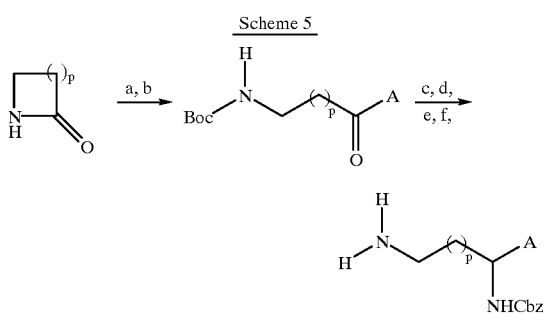

(a) di-t-butyl dicarbonate, DMAP, THF; (b) A*Li; (c) hydroxylamine hydrochloride (d) H₂ Pd/C e) CbzCl (f) HCl/dioxane.
*see generic claims for A = alkyl, aryl, heteroaryl, alkaryl, alkheteroaryl.

Scheme 6

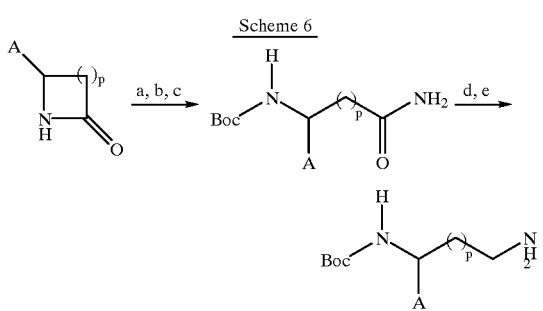

(a) di-t-butyl dicarbonate, DMAP, THF; (b) LiOH; (c) i-butyl chloroformate, ammonia (d) trifluoroacetic anhydride, Et₃N (e) H₂/Pd.

Scheme 7

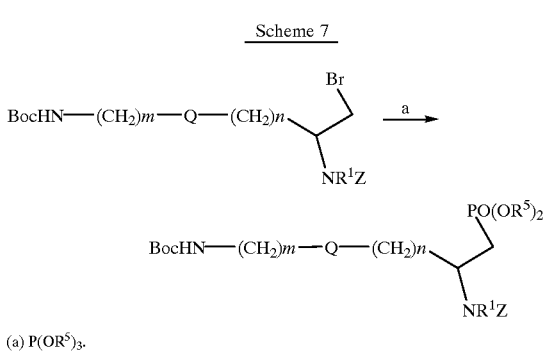

(a) P(OR⁵)₃.

Scheme 8

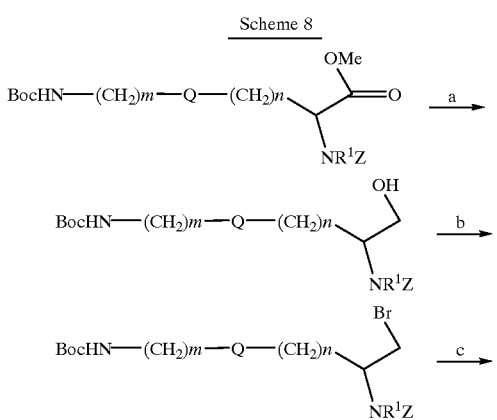

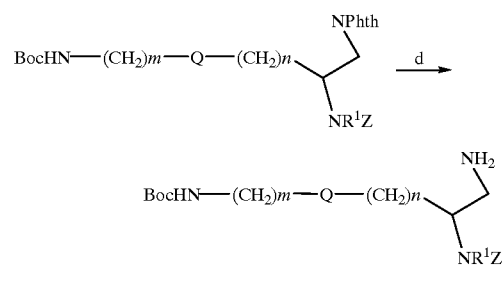

(a) DIBAL-H, toluene, -70° C., 1 h; (b) Ph₃PBr₂, DMAc, 16 h; (c) K⁺NPhth, THF; (d) NH₂NH₂, EtOH.

Scheme 9

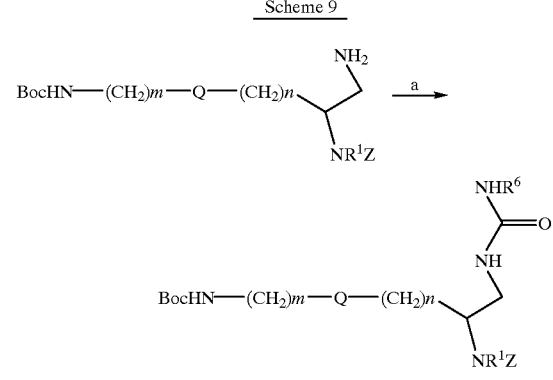

(a) O=C=NR⁶, DCM.

Scheme 10

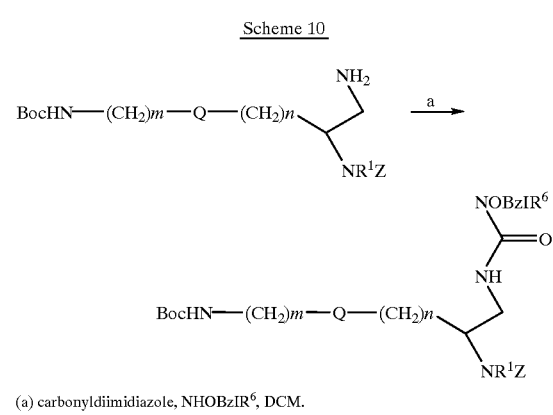

(a) carbonyldiimidazole, NHOBzIR⁶, DCM.

Scheme 11

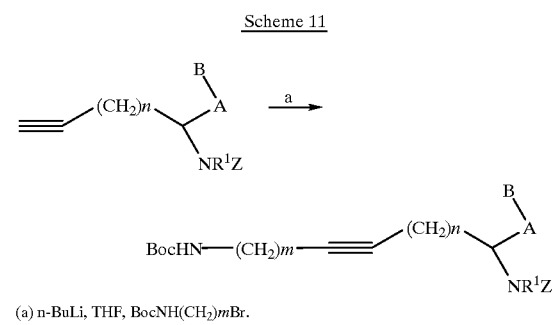

(a) n-BuLi, THF, BocNH(CH₂)mBr.

Scheme 12
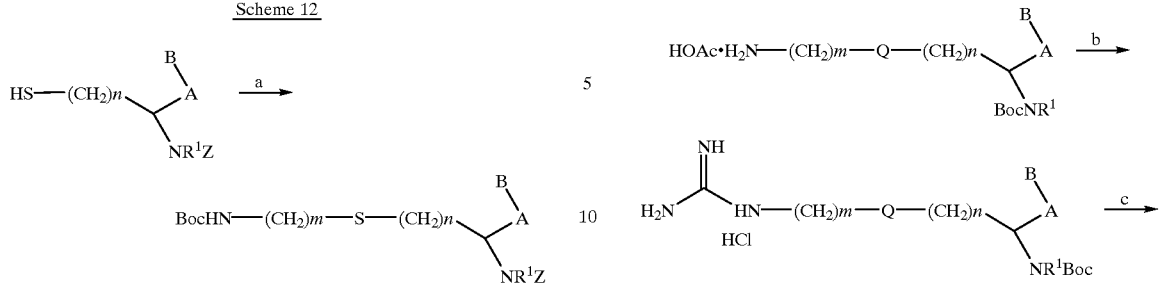
(a) NaOMe, THF, BocNH(CH$_2$)$m$Br.
Scheme 13
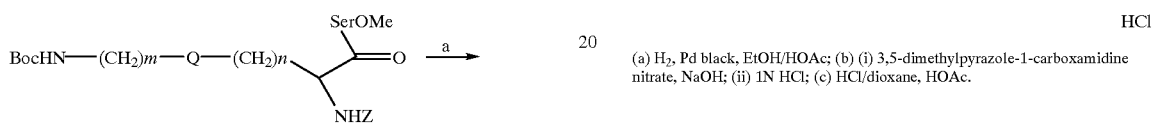
(a) H$_2$, Pd black, EtOH/HOAc; (b) (i) 3,5-dimethylpyrazole-1-carboxamidine nitrate, NaOH; (ii) 1N HCl; (c) HCl/dioxane, HOAc.
Scheme 15
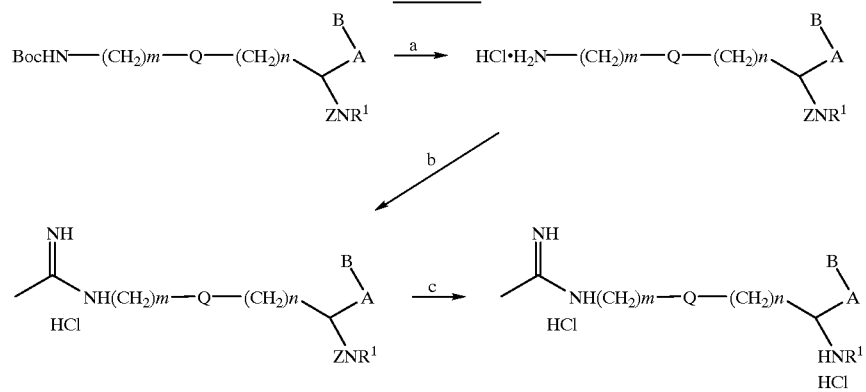
(a) HCl/dioxane, HOAc; (b) (i) methyl acetimidate, NaOH; (ii) 1N HCl; (c) H$_2$, Pd black, EtOH, HOAc.
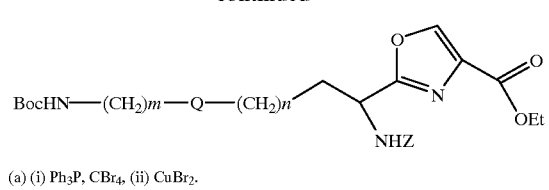
(a) (i) Ph$_3$P, CBr$_4$, (ii) CuBr$_2$.
Scheme 14
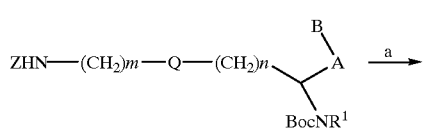
Scheme 16
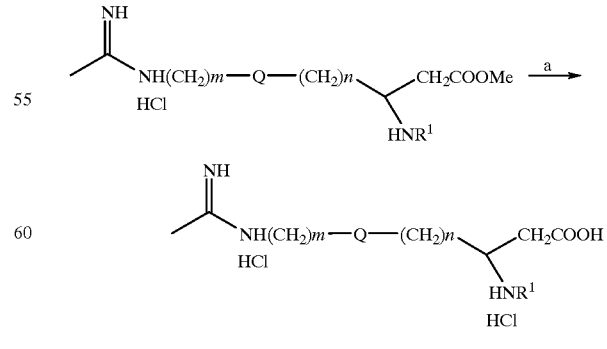
(a) 2N HCl, Δ

Scheme 17

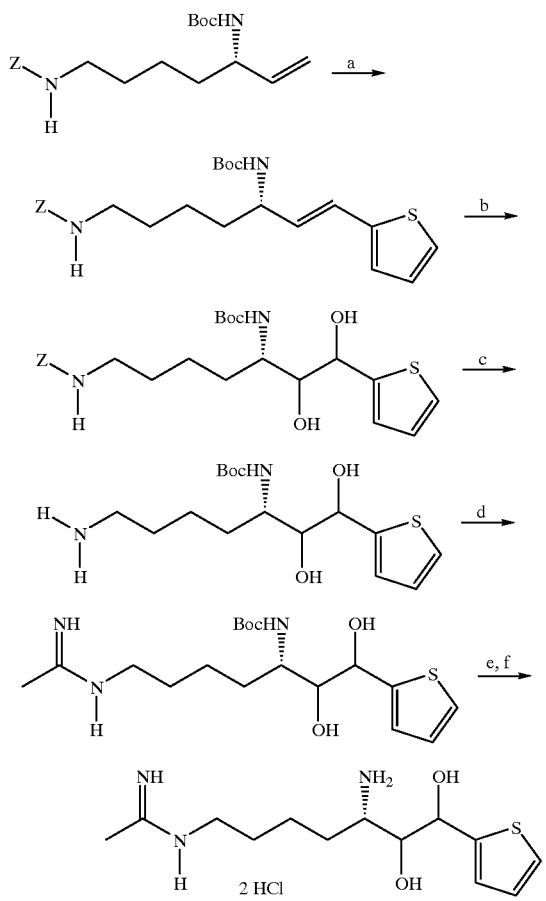

(a) Pd(OAc)$_2$/tri-o-tolylphosphine/2-bromothiophine/triethylamine;
(b) OsO$_4$, NMMO, acetone-H$_2$O; (c) H$_2$/Pd/AcOH;
(d) ethyl acetimidate HCl/EtOH; (e) HCl/Dioxane/AcOH; (f) HCl/H$_2$O.

Scheme 18

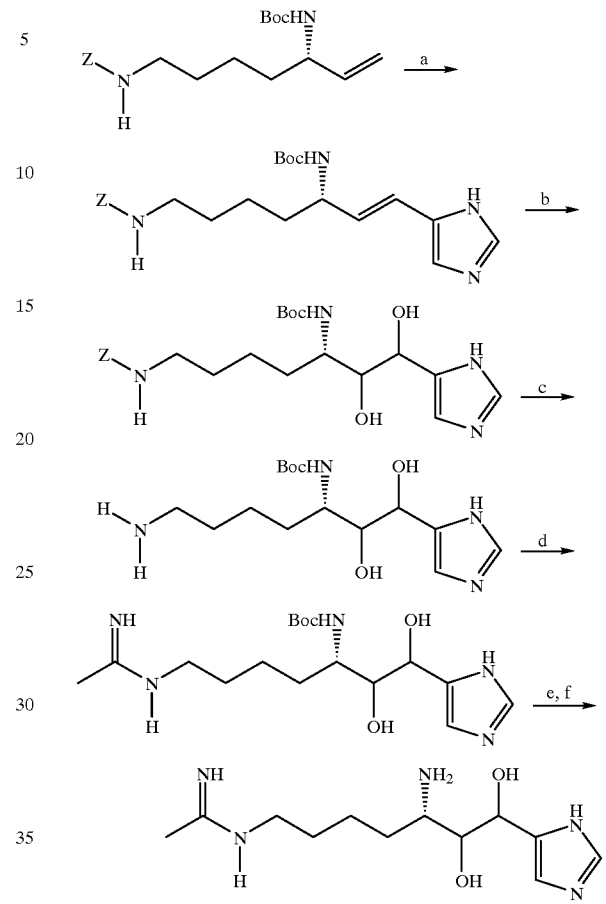

(a) Pd(OAc)$_2$/tri-o-tolylphosphine/4-bromoidazole/triethylamine; (b) OsO$_4$, NmMO;
(c) H$_2$/Pd/AcOH; (d) ethyl acerimidate HCl/EtOH; (e) HCl/Dioxane/AcOH; (f) HCl/H$_2$O.

Scheme 19

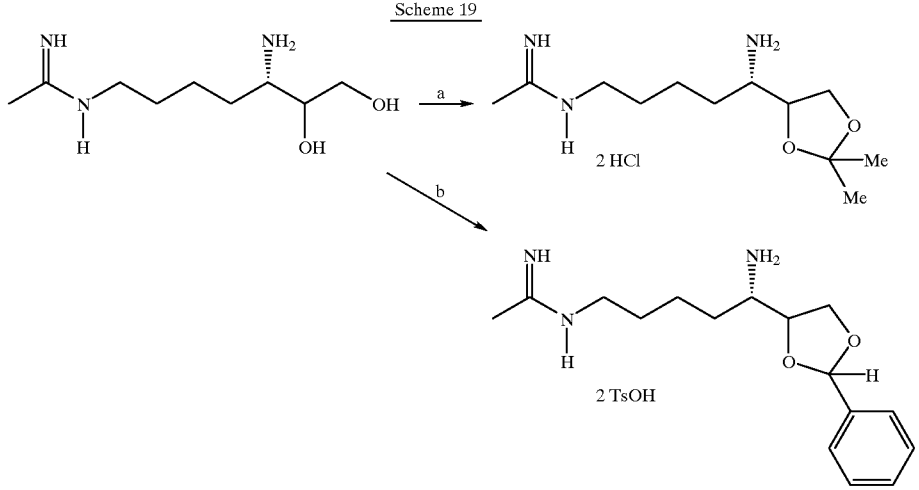

(a) 2,2-dimethoxypropane/DMF/HCl/Dioxane; (b) 1,1,1-trichloroethane/TsOH/benzaldehyde.

Scheme 20
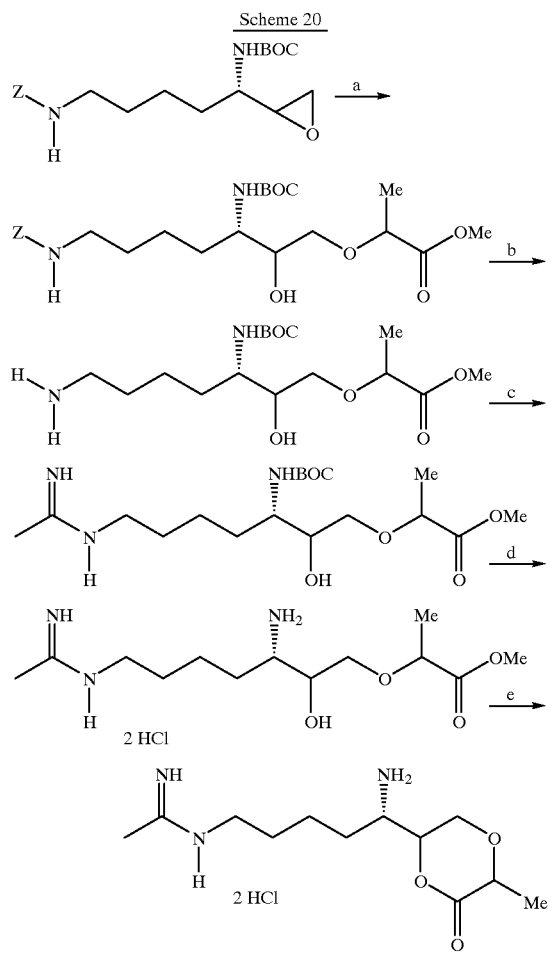
(a) NaH/DMF/ZnCl$_2$/THF/methyl lactate; (b) H$_2$/Pd/AcOH; (c) ethyl acetimidate HCl/EtOH; (d) HCl/Dioxane/AcOH; (e) HCl/H$_2$O.
Scheme 21
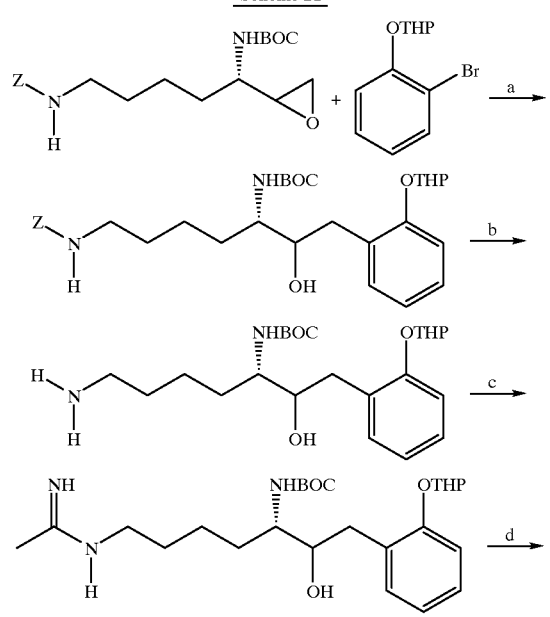
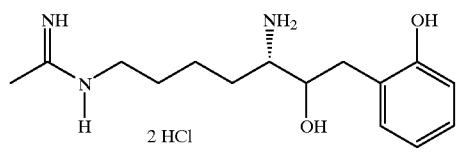
(a) n-BuLi/THF/-78° C.; (b) H$_2$/Pd/AcOH; (c) ethyl acetimidate HCl/EtOH; (d) HCl/Dioxane/AcOH.
Scheme 22
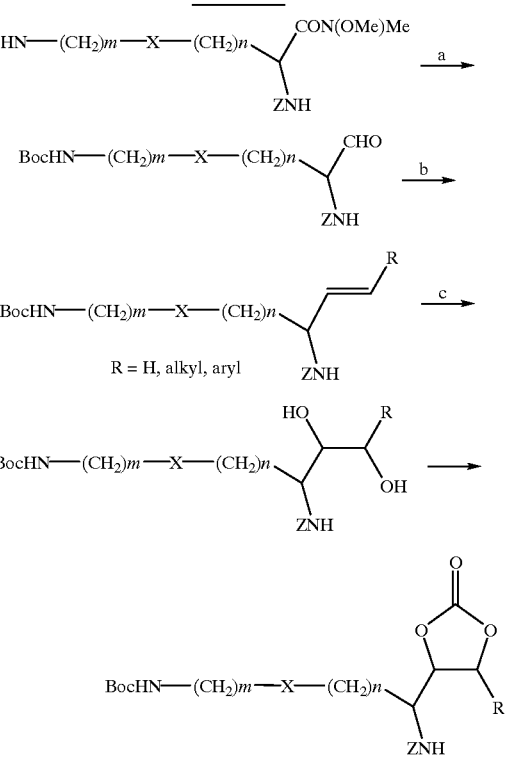
(a) LiAlH$_4$, THF, 0° C.–20° C.; (b) RCH=PPh$_3$, THF; (c) OsO$_4$, NMMO acetone-H$_2$O; (d) Cl$_2$C=O, pyridine
Scheme 23
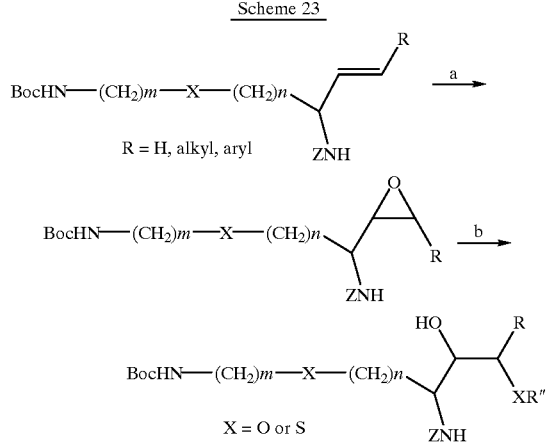
(a) mcpba, DCM, 20° C.; (b) NaSR″ or NaOR″, toluene-THF, Lewis acid.

Scheme 24

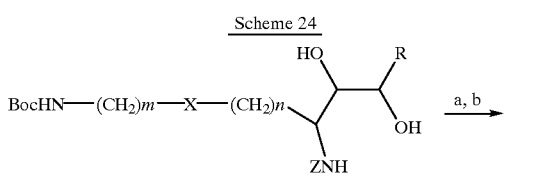

(a) TrCl, pyridine 20° C.; (b) Et$_2$NSF$_3$, dioxane.

Scheme 25

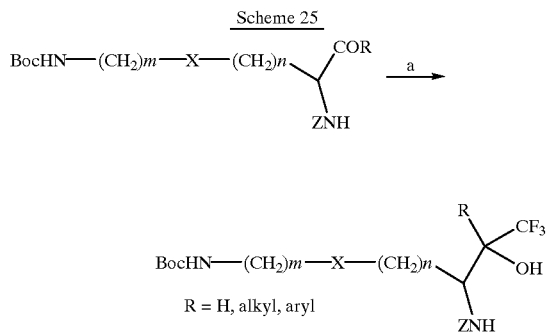

R = H, alkyl, aryl (a) CF$_3$I, Zn, DMF, -20° C.

Scheme 26

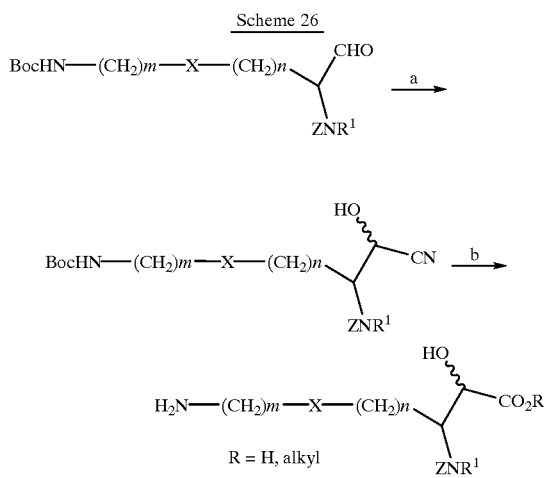

R = H, alkyl (a) KCN, NaHSO$_4$; (b) ROH, HCl or H$_2$O, H$^+$.

Scheme 27

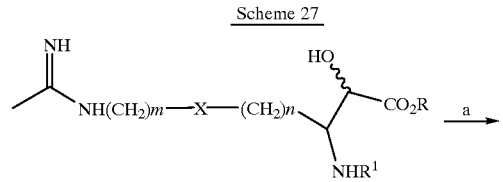

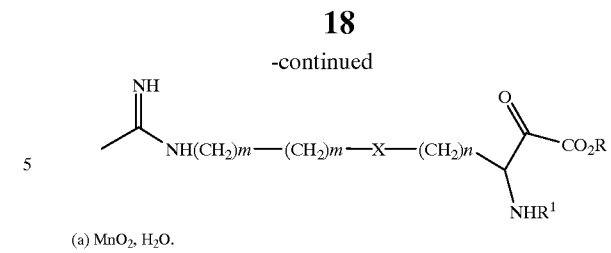

(a) MnO$_2$, H$_2$O.

Scheme 28

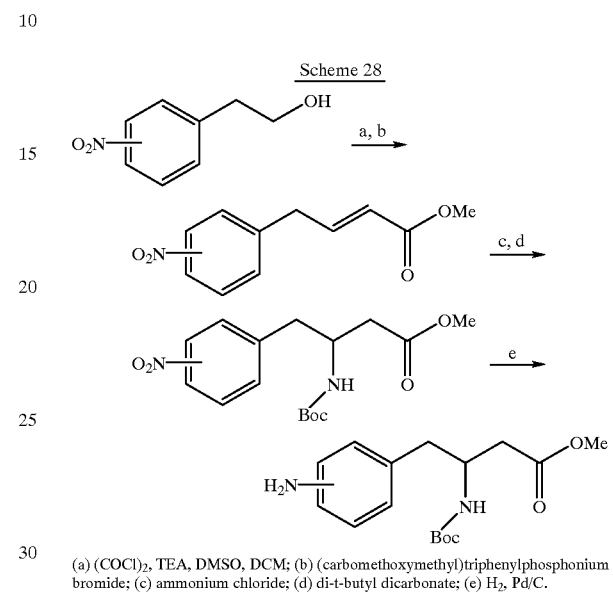

(a) (COCl)$_2$, TEA, DMSO, DCM; (b) (carbomethoxymethyl)triphenylphosphonium bromide; (c) ammonium chloride; (d) di-t-butyl dicarbonate; (e) H$_2$, Pd/C.

Without further elaboration, it is believed that one skilled in the art can, using the preceding description, utilize the present invention to its fullest extent. Therefore the following preferred specific embodiments are to be construed as merely illustrative and not limitative of the remainder of the disclosure in any way whatsoever.

All experiments were performed under either dry nitrogen or argon. All solvents and reagents were used without further purification unless otherwise noted. The routine work-up of the reactions involved the addition of the reaction mixture to a mixture of either neutral, or acidic, or basic aqueous solutions and organic solvent. The aqueous layer was extracted n times (x) with the indicated organic solvent. The combined organic extracts were washed n times (x) with the indicated aqueous solutions, dried over anhydrous Na$_2$SO$_4$, filtered, concentrated in vacuo, and purified as indicated. Separations by column chromatography were achieved with conditions described by Still. (Still, W. C.; Kahn, M.; Mitra, A. Rapid Chromatograhic Technique for Preparative Separation with Moderate Resolution. *J. Org. Chem.*, 1978, 43, 2923–2925.) The hydrochloride salts were made from 1N HCl, HCl in ethanol (EtOH), 2 N in MeOH, or 6 N HCl in dioxane. Thin layer chromatograms were run on 0.25 mm EM precoated plates of silica gel 60 F254. High performance liquid chromatograms (HPLC) were obtained from C-8 or C-18 reverse phase columns which were obtained from several vendors. Analytical samples were dried in an Abderhalden apparatus at either 56° C. or 78° C. $^1$H NMR spectra were obtained from either General Electric QE-300 or Varian VXR 400 MHz spectrometer with tetramethylsilane as an internal standard. $^{13}$C NMR were obtained from a Varian spectrometer at 125.8 MHz with tetramethylsilane as an internal standard.

EXAMPLE 1

3S-amino-7-[(1-iminoethyl)amino]heptanoic Acid

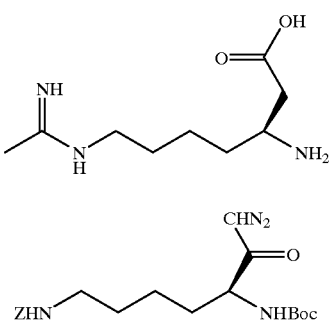
1a

1a. Boc-L-Lys(Z)-OH in 50 mL THF (3.8 g, 10 mmol) was reacted with isobutyl chloroformate (1.4 mL, (10 mmol) in the presence of NMM (1.1 mL, 10 mmol). The salt was filtered and the mixed anhydride was reacted with 25 mmol diazomethane in 100 mL Et$_2$O for 12 h. Solvent was evaporated to give an oil. This structure and subsequent structures were characterized by $^1$H NMR.

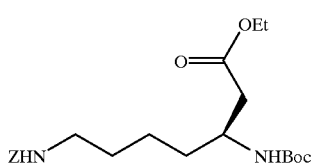
1b 1b. 1a dissolved in 50 mL EtOH was treated with Ag benzoate (0.5 g) in the presence of TEA (5 mL) for 2 h. After filtration, the β-amino acid ester was purified by column chromatography to give 0.84 g of product.

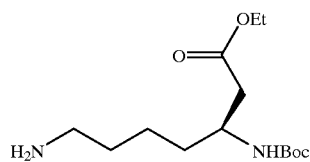
1c 1c. 1b (0.84 g 12 mmol) dissolved in 30 mL MeOH was reduced in the presence of 1 g ammonium formate and 0.2 g Pd black for 60 min. After filtration and evaporation, product was recovered.

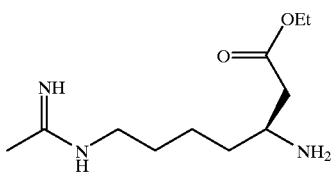
1d

Ethyl 3S-amino-7-[(1-iminoethyl)amino]heptanoate
1d. 1c in 10 mL DMF was treated with methyl acetimidate (0.692 g, 6 mmol) and N,N-diisopropylethylamine (1.05 mL, 6 mmol) overnight. Solvent was removed in vacuo and the residue treated with TFA (10 mL) for 30 min. The reaction was diluted with H$_2$O and purified by HPLC to yield 0.16 g (35.1%) of an oil. FAB MS: MH$^+$=230.2

1. 1d (0.12 g, 0.52 mmol) dissolved in 20 mL 2N HCl was refluxed for 60 min. The reaction was diluted with H$_2$O and lyophilized to yield 0.107 g (100%) of an oil. FAB MS: MH$^+$=202.3

EXAMPLE 2

3S-amino-6-[(1-iminoethyl)amino]hexanoic Acid

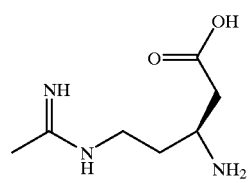
2

2. Example 2 was prepared in the same manner as described for example 1 starting with Boc-Orn(Z)-OH (3.6 g, 10 mmol) to yield 0.123 g (33%) of an oil. FAB MS: MH$^+$=188.0

EXAMPLE 3

N-(5S-amino-6,7-dihydroxyheptyl)ethanimidamide, dihydrochloride

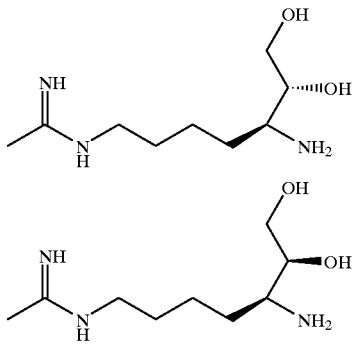

The absolute stereochemistry of the hydroxyl group at position C-6 has not been determined. The diastereomers have been separated as described below A difference in the biological activity between the diastereomers is seen.

N-α-Boc-N-ε-Z-L-Lys-OMe (3a)

3a. To a stirring solution of cesium carbonate (32.6 g, 0.10 mol) in 150 mL DMF was added N-α-Boc-N-ε-Z-Lys (68.3 g, 0.18 mol). After 10 min, iodomethane (51.1 g, 0.36 mol) was added. After 18 h, solvent was removed in vacuo. The resultant gum was washed with hexane and the hexane was decanted. The product was dissolved in 100 mL of DCM and filtered through a 100×70 mm pad of EM silica gel. The silica was washed with 900 mL DCM and 300 mL EtOAc which were combined. The solvent was removed in vacuo to yield 66.4 g (94%) of product.

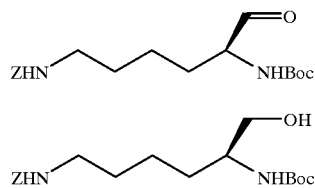

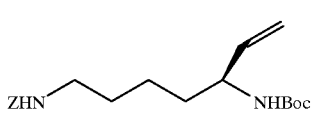

3b, c. To a stirring solution of 3a (7.9 g, 20 mmol) in 100 mL dry toluene cooled to −70° C. was added dropwise over 10 min 1M DIBAL-H in toluene (40 mL, 40 mmol). After stirring an additional 20 min, the reaction was quenched with 4 mL MeOH. Upon removal of the ice bath, 150 mL of saturated solution of Rochelle salt was added to the reaction. After stirring for 1 h, the layers were separated. The aqueous layer was extracted with 2×150 mL EtOAc. The combined organic layers were washed with 2×200 mL $H_2O$, dried, filtered, and concentrated in vacuo. The residue was purified by flash chromatography according to Still et al. to yield 5.37 g (74%) of 3b and 0.70 g (10%) of 3c. Both 3b and 3c were white solids.

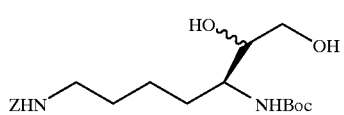

3d. To a stirring suspension of methyltriphenylphosphonium bromide (2.18 g, 6.1 mmol) in 50 mL of $Et_2O$ was added dropwise 0.5 M potassium hexamethyldisilazide in toluene (12.2 mL, 6.1 mmol). After stirring for 1.5 h, 3b (2.22 g, 6.1 mmol) in 50 mL of $Et_2O$ was added. After 16 h, a white solid was filtered from the reaction. The filtrate was concentrated in vacuo. The residue was purified by flash chromatography to yield 1.11 g (50%) of 3d, a clear colorless gum. Anal calcd for $C_{20}H_{30}N_2O_4.O_2$ $H_2O$: C, 65.62; H, 8.37; N, 7.65. Found: C, 65.65; H, 8.07; N, 7.59.

3e

3e. To a stirring solution of 3d (1.20 g, 3.3 mmol) in 80 mL of acetone:$H_2O$ (3:1) was added 4-methylmorpholine N-oxide (0.64 g, 4.8 mmol) and 2.5% $OsO_4$ in t-BuOH (3.4 mL, 3.4 mmol). After 18 h, 120 mL of $H_2O$, 8 g of celite, and 1.6 g $Na_2S_2O_4$ were added to the reaction. The reaction was filtered through a pad of wet celite. To the filtrate was added 200 mL of 1M $KHSO_4$. The filtrate was extracted with 3×200 mL EtOAc. The combined organic layers were dried, filtered, and stripped. The residue was purified by flash chromatography to yield 0.93 g (71%) of 3e. Anal calcd for $C_{20}H_{32}N_2O_6.0.25$ $H_2O$: C, 59.91; H, 8.17; N, 6.99. Found: C, 59.75; H, 8.42; N, 6.77.

(3f)

3f. Benzyloxycarbonyl protecting group was removed from 3e (1.38 g, 3.5 mmol) by catalytic hydrogenation using Pd black as the catalyst yielding 3f quantitatively.

3A, 3B. To a stirring solution of 3f (3.90 g, 14.9 mmol) and TEA (3.3 mL, 24 mmol) in 10 mL of DMF was added methyl acetimidate (2.44 g, 22.2 mmol). After 16 h, TEA.HCl was filtered from the reaction and washed with a minimum of DMF. The filtrate was adjusted to pH 3 with 1N HCl. The filtrate was concentrated under high vacuum. The residue was applied to a reverse phase column (YMC AQ-363-10P, ODS) using a gradient of 20% $CH_3CN$/0.025% HOAc to 50% $CH_3CN$/0.025% HOAc. The two diastereomers were separated. The first eluting isomer was treated with 1N HCl for 1 h at ambient temperature. The aqueous solution was lyophilized. The yield was 0.51 g of 3A. The second eluting isomer was treated in the same fashion to yield 0.40 g of 3B. Anal calcd for (3B) $C_9H_{21}N_3O_2.1.75$ HCl.0.75 $H_2O$: C, 38.52; H, 8.71; N, 14.97. Found: C, 38.60; H, 8.73; N, 13.34

EXAMPLE 4

Ni-(1-iminoethyl)-1,4-pentanediamine, dihydrochloride

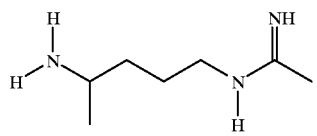

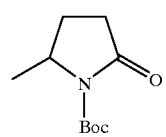

4a. A solution of 5-methyl-2-pyrrolidinone (50 g, 0.5 mol), di-t-butyl dicarbonate (165 g, 0.76 mol), DMAP (62 g, 0.5 mol) and $Et_3N$ (250 mL) in $CH_2Cl_2$ (250 mL) was stirred at room temperature for 24 h. The solvent was concentrated in vacuo and the resulting oily red solid suspended in $Et_2O$ and filtered. The $Et_2O$ solution was passed through a pad of silica gel. The solvent was removed to yield an orange liquid. The product was chromatographed to yield 82 g (83%) of a yellow liquid.

4b

4b. Sodium hydroxide (2.24 g, 56 mmol) was added to a stirring solution of 4a (4.0 g, 20 mmol) in THF:$H_2O$ (175 mL:75 mL). The resulting solution was stirred for 2 h. The solvent was concentrated in vacuo to 75 mL. The solution was acidified with citric acid (1 M, 75 mL), extracted with EtOAc (200 mL), dried, and concentrated in vacuo to yield 5.36 g of an oil. The product was crystallized from Et$_2$O/hexane to yield 4.24 g (98%) of a white solid.

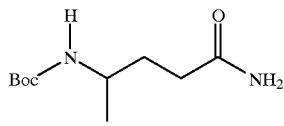

4c

4c. To a stirred solution of 4b (4.0 g, 18 mmol) and TEA (2.6 mL, 18 mmol) in THF (50 mL) at −10° C. was added isobutyl chloroformate (2.39 mL, 18 mmol) dropwise and the solution stirred for 20 min. Ammonium hydroxide (3.9 mL, 28%) was added and the resulting solution was stirred for 18 h allowing to warm to room temperature. The solution was concentrated in vacuo and the residue suspended in boiling EtOAc (80 mL) and filtered. This was repeated. The filtrate was concentrated to 30 mL and the solid collected to yield 3.82 g.

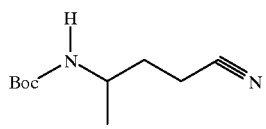

4d

4d. To a stirred solution of 4c (3.5 g, 16 mmol) in THF (20 mL) at 0° C. was added TFAA (2.5 mL, 17.5 mmol) dropwise and the solution stirred for 20 min. The solution was poured onto Et$_2$O (125 mL) and NaHCO$_3$ (satd, 25 mL), the layers separated and the organic solution extracted with NaHCO$_3$ (satd) and brine (satd.), dried, filtered, and concentrated in vacuo to yield 2.88 g of an oil. The product was vacuum distilled (bp 130° C. @ 0.6 mmHg) to yield 2.2 g (69%) of a yellow liquid.

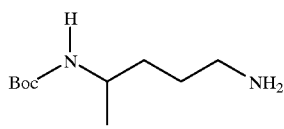

4e

4e. A solution of 4d (1.7 g, 8.6 mmol) in EtOH was treated with H$_2$ (300 psi) over Raney nickel at 50° C. for 8 h. The reaction mixture was filtered and concentrated in vacuo to yield 1.25 g (73%) of a colorless oil.

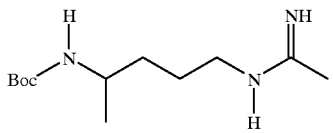

4f

4f. A solution of 4e (1.0 g, 4.9 mmol) and ethyl acetimidate hydrochloride (0.62 g, 5 mmol) in anhyd. EtOH (25 mL) was stirred for 18 h. The reaction solution was concentrated in vacuo to yield 1.46 g of a white foam. This material was used in the next step without further purification.

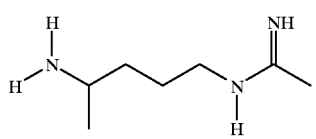

4

4. A solution of 4f (1.46 g, 4.9 mmol) in acetone (25 mL) was treated with HCl (10 mL, 2 M in MeOH), and stirred for 10 min. The reaction mixture was concentrated in vacuo and triturated with ethanol and THF to yield an oil. Crystallization of the oil was attempted from i-propanol. The solution was concentrated in vacuo to obtain a foam 0.42 g (39%) which was dried. Anal. Calcd for C$_7$H$_{17}$N$_3$.2 HCl. 0.15 H$_2$O.0.15 i-PrOH: C, 39.27; H, 9.07; N, 18.44; Cl, 31.12. Found: C, 39.25; H, 9.53; N, 18.04; Cl, 31.52.

EXAMPLE 5

N1-(1-iminoethyl)-1,5-heptanediamine

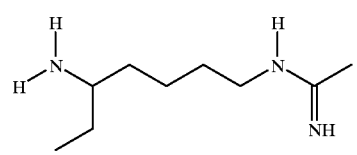

5

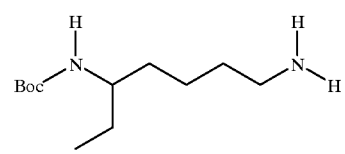

5a

5a. A solution of 3d (500 mg, 1.38 mmol) in AcOH/EtOH was treated with H$_2$ (5 psi) over Pd black for 21 h. The reaction mixture was filtered and concentrated in vacuo. The residue was dissolved in CH$_2$Cl$_2$ (125 mL) and extracted with NaOH (1 M), dried over Na$_2$SO$_4$, filtered, and concentrated in vacuo to yield 0.32 g of a white gum.

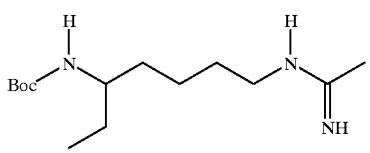

5b

5b. A solution of 5a (0.29 g, 1.26 mmol) and ethyl acetimidate hydrochloride (0.156 g, 1.3 mmol) in EtOH (15 mL) was stirred for 18 h. The reaction solution was concentrated in vacuo to yield 0.40 g of a white gum. This material was used in the next step without further purification.

5. To a stirred solution of 5b (0.40 g, 1.26 mmol) in AcOH (glacial, 10 mL) was added HCl (6.95 M in dioxane, 14 mmol). The resulting solution was stirred for 2 h. The solution was concentrated in vacuo to yield 0.41 g of a gum. This material was purified by reversed phase HPLC on a C-18 support (7:3 CH$_3$CN:H$_2$O) to yield 95 mg of clean product as a glass. HRMS calcd for C$_9$H$_{22}$N$_3$: 172.1814. Found: 172.1809.

EXAMPLE 6

N1-(1-iminoethyl)-5-phenyl-1,5-pentanediamine

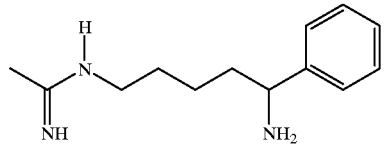

6

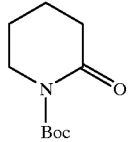

6a

6a. The reaction for example 4a was repeated on a 0.4 mol scale with valerolactam. The yield of the reaction was quantitative.

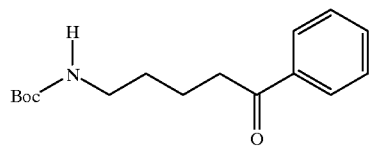

6b

6b. A solution of 6a (5 g, 25 mmol) in THF (125 mL) at −78° C. was treated with phenylmagnesium bromide (9.5 mL, 3.0 M). The resulting solution was stirred at −72° C. for 35 min then poured onto brine (satd) and extracted with Et$_2$O. The organic solution was dried, filtered, and concentrated in vacuo to yield 6.42 g of an oil. The product was chromatographed and recrystallized from hexane to yield 3.78 g (55%) of a white solid. Anal. Calcd for C$_{16}$H$_{23}$NO$_3$: C, 69.28; H, 8.36; N, 5.05. Found: C, 69.30; H, 8.84; N, 4.95.

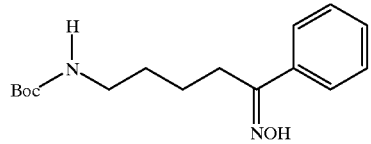

6c

6c. A stirred suspension of 6b (0.50 g, 1.8 mmol) in EtOH (3 mL) was treated with a solution of hydroxylamine hydrochloride (0.25 g, 3.6 mmol), sodium acetate (0.25 g, 3.8 mmol) in H$_2$O (3 mL). The solution was refluxed for 4.5 h, during which time a solution formed. After cooling to room temperature H$_2$O (50 mL) was added and the mixture extracted with CHCl$_3$ (3×30 mL). The CHCl$_3$ extracts were combined, dried, filtered, and concentrated in vacuo to yield 420 mg (80%) of a white solid. Anal. Calcd for C$_{16}$H$_{24}$N$_2$O$_3$: C, 65.73; H, 8.27; N, 9.50. Found: C, 65.79; H, 8.79; N, 9.53.

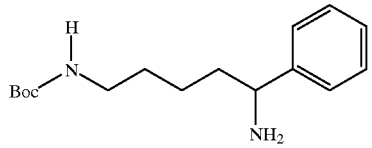

6d

6d. A solution of 6c (3.54 g, 24 mmol) in EtOH was treated with H$_2$ (5 psi) over 10% Pd/C for 24 h. The reaction mixture was filtered and concentrated in vacuo to yield 2.61 g (77%) of a colorless oil. Anal. Calcd for C$_{16}$H$_{26}$N$_2$O$_2$:. 0.4 EtOH: C, 67.98; H, 9.64; N, 9.44. Found: C, 68.19; H, 9.38; N, 9.11.

6e

6e. To a solution of 6d (2.1 g, 7.54 mmol) in EtOAc (100 mL) in a separatory funnel was added NaOH (1 M, 60 mL) and benzylchloroformate (1.93 g, 11.31 mmol). The mixture was shaken for several minutes and the layers separated, The EtOAc solution was extracted with brine, dried, filtered, and concentrated in vacuo to yield an oil. The oil was chromatographed to yield 2.34 g (75%) of a white solid.

6f

6f. A solution of 6e (2.0 g, 4.85 mmol) in CH$_2$Cl$_2$ (25 mL) at 0° C. was treated with TFA (20 mL) and allowed to warm to room temperature over 1.5 h. The solution was concentrated in vacuo to yield a yellow oil. The oil was dissolved in CHCl$_3$ and extracted with NaOH (1 M) and brine (satd), dried over Na$_2$SO$_4$, filtered, and concentrated in vacuo to yield 1.35 g (89%) of a gum.

6g

6g. A solution of 6f (1.3 g, 4.16 mmol) and ethyl acetimidate hydrochloride (0.533 g, 4.2 mmol) in EtOH (20 mL) was stirred for 18 h. The reaction solution was concentrated in vacuo to yield 1.65 g of a white foam. This material was purified by reversed phase HPLC to yield 1.09 g of a foam. Anal. Calcd for C$_{21}$H$_{27}$N$_3$O$_2$.1 HCl.0.75 H$_2$O: C, 62.52; H, 7.37; N,10.42. Found: C, 62.82; H, 7.05; N, 10.12.

6. A solution of 6g (0.94 g, 2.41 mmol) in AcOH was treated with H$_2$ (5 psi) over Pd black for 20 h. The reaction mixture was filtered and concentrated in vacuo. The residue was dissolved in EtOH (10 mL) and HCl/Dioxane (1 mL, 5.8 M) added and concentrated in vacuo to yield 0.52 g (74%) of a white powder. Anal. Calcd for $C_{13}H_{21}N_2O_2 \cdot 2\ HCl \cdot 0.75\ H_2O \cdot 0.2\ EtOH$: C, 51.10; H, 8.22; N, 13.34; Cl, 22.51. Found: C, 50.98; H, 7.82; N, 13.66; Cl, 22.20.

EXAMPLE 7

N-[5-amino-5-(2-hydroxyphenyl)pentyl]ethanimidamide

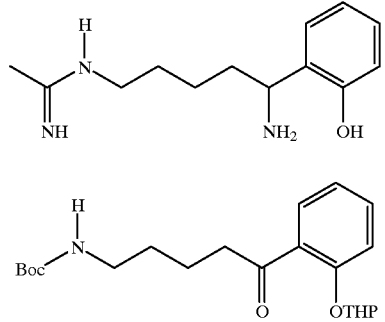

7a. The reaction for example 6b was repeated on a 25 mmol scale with 2-(tetrahydropyran-2-yloxy)phenyllithium. The 2-(tetrahydropyran-2-yloxy)phenyllithium was prepared from 2-(tetrahydropyran-2-yloxy)phenyl bromide and n-BuLi in THF at −78° C. The crude product was chromatographed to yield 4.07 g (43%) of a yellow oil.

7. Example 7 is prepared in the same manner as described for example 6.

EXAMPLE 8

N-[5-amino-5-(4-hydroxyphenyl)pentyl]ethanimidamide

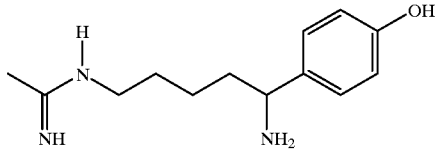

8. Example 8 is prepared in the same manner as described for example 6 starting with 4-(tetrahydropyran-2-yloxy)phenyllithium.

EXAMPLE 9

N-(5-aminononyl)ethanimidamide

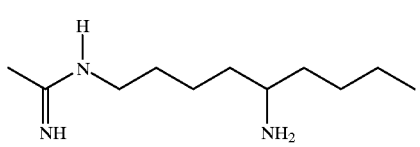

9. Example 9 is prepared in the same manner as described for example 6 starting with n-butyllithium.

EXAMPLE 10

β-amino-4-[(1-iminoethyl)amino]benzenepropanoic acid, dihydrochloride hydrate

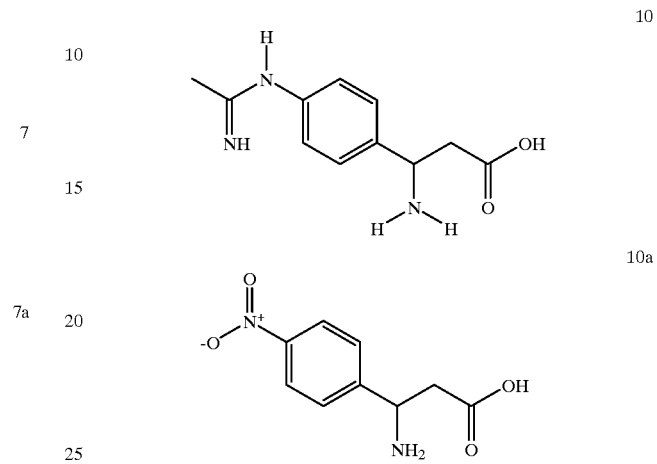

10a. A mixture of 4-nitrobenzaldehyde (39 g, 0.26 mol), malonic acid (30.5 g, 0.29 mol) and ammonium acetate (49 g, 0.64 mol) in AcOH was heated at 100° C. for 5 h, followed by the addition of HCl (25%, 200 mL) and continued heating at 100° C. for 5 additional hours. The reaction mixture was cooled to room temperature and $H_2O$ (300 mL) added, the resulting precipitate was filtered and washed with $H_2O$ (100 mL). The filtrate and wash were combined and concentrated in vacuo, followed by the addition of $H_2O$ (300 mL). The resulting mixture was heated on a steam bath, decolorized with carbon and filtered through celite. The pH of the solution was adjusted to 7 with $NH_4OH$ (conc.) and the resulting precipitate collected. The solid was washed with $H_2O$ (100 mL), methanol:$H_2O$ (1:1, 100 mL), methanol:$Et_2O$ (1:1, 100 mL) and $Et_2O$ (100 mL). The solid was dried in vacuo to yield 29.8 g of a yellow solid.

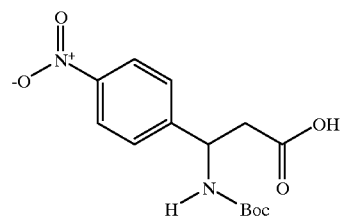

10b. A solution of 10a (5.0 g, 24 mmol), di-t-butyl dicarbonate (5.7 g, 26 mmol) in NaOH (1 M, 50 mL) and dioxane (50 mL) was stirred for 4 h. The solvent was concentrated to 50 mL to which was added EtOAc (400 mL) and $KHSO_4$ (1M, 75 mL). The layers were separated and the organic layer was washed with brine (satd.), dried, filtered, and concentrated in vacuo to yield 8.5 g of a yellow foam.

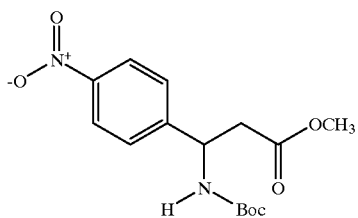

10c

10c. Example 10c was prepared in the same manner as 3a.

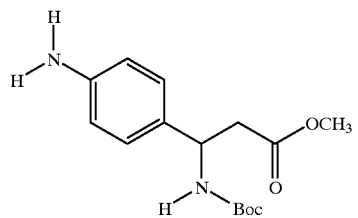

10d

10d. A solution of 10c (8 mmol) in EtOH was treated with H$_2$ (5 psi) over 10% Pd/C for 18 h. The reaction mixture was filtered and concentrated in vacuo to yield the product.

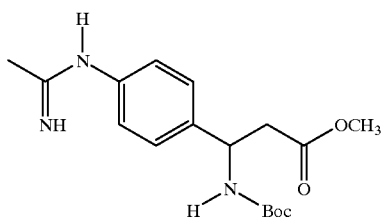

10e

10e. The reaction for example 6g was repeated using 10d on a 5 mmol scale.

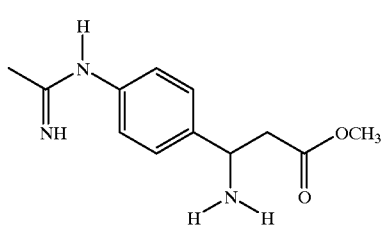

10f

10f. A solution of 10e (890 mg, 2.4 mmol) in CH$_2$Cl$_2$ : TFA (1:1, 50 mL) was stirred at 0° C. for 15 min. The solvent was removed in vacuo and the residue was dissolved in water (100 mL) and the extracted with EA. The pH of the aqueous solution was adjusted to 11 with K$_2$CO$_3$ and extracted with CH$_2$Cl$_2$. The CH$_2$Cl$_2$ extracts were dried (Na$_2$SO$_4$) and concentrated. The residue was chromatographed on silica gel (9:1:1; ACN:H$_2$: AcOH) to to yield 10f 50 mg (5%) as a foam. Anal. Calcd for C$_{12}$H$_{17}$N$_3$O$_2$.3 AcOH.1 H$_2$O: C, 49.87; H, 7.21; N,9.69. Found: C, 49.61; H, 6.96; N, 9.78. HRMS calcd.: 235.1320. Found: 235.1320.

10. A solution of 10f (20 mg, 0.5 mmol) in HCl (2N, 5 mL) was refluxed for 1 h. The solvent was removed via lyophilization to yield 10 24 mg as a foam. Anal. Calcd for C$_{11}$H$_{15}$N$_3$O$_2$.2.3 HCl.0.6 H$_2$O: C, 41.82; H, 5.90; N,13.30.

EXAMPLE 11

α-[1-amino-5-[(1-iminoethyl)amino]pentyl] benzenemethanol hydrochloride dihydrate

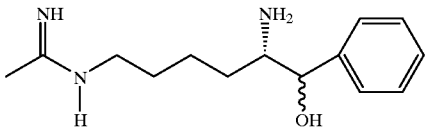

11

N-α-Z-N-ε-Boc-L-Lys-N(OMe)Me     (11a)

11a. To a stirring solution of N-(X-Z-E-Boc-L-Lys (5 g, 13.8 mmol), N,O-dimethylhydroxylamine HCl (3.9 g, 39.5 mmol),1-hydroxybenzotriazole hydrate (2 g, 14.5 mmol), and triethylamine (13.2 g, 17 mL, 130 mmol) in 75 mL of dimethylformamide (DMF) cooled in an ice bath was added EDC (2.8 g, 14.5 mmol). After stirring 55 h at ambient temperature, triethylamine hydrochloride was filtered from the reaction mixture and the filtrate was concentrated in vacuum. The residue was distributed between 150 mL of ethyl acetate (EtOAc) and 75 mL of 1M KHSO$_4$ solution. The layers were separated. The organic layer was washed with ×75 mL of saturated KHCO$_3$ solution and 1×75 mL of brine and was worked up in the usual manner giving 5.3 g of 11a (95%).

11b. To a stirring solution of 11a (1.8 g, 4.26 mmol) and N,N,N,N-tetramethylethylendiamine (1.63 g, 2.12 mL, 14.06 mmol) in 50 mL of dry THF at −72° C. was added phenyllithium, 1.8 M solution in cyclohexane, (1.18 g,7.8 mL, 14.06 mmol). After stirring at the same temperature for 2.5 h, the reaction mixture was added to 50 mL of 1M KHSO$_4$ solution and 50 mL of EtOAc. The layers were separated, the organic layer was washed with 1×30 mL of brine and worked up in the usual manner giving 2.8 g of crude product which was purified using column chromatography. The yield of 11b was 1.3 g (69.5%).

11c. To example 11b (1.3 g, 2.96 mmol) dissolved in 30 mL of acetic acid was added 3 mL of 5N HCl/dioxane. The reaction was stirred for 20 min. at ambient temperature concentrated under vacuum. The residue was dried, treated with Et$_2$O, washed with hexane, and dried yielding 1.0 g (90.9%) of 11c. Anal.calcd. for C$_{20}$H$_{24}$N$_2$O$_3$.HCl.0.4 H$_2$O: C, 62.54; H, 6.77; N, 7.29; CL, 9.23. Found: C, 62.88; H, 6.80; N, 7.22; Cl, 9.18.

11d. 0.5 g of 11c dissolved in 10 mL of water was neutralized with Na$_2$CO$_3$ (pH-9–10), the oil was extracted with 3×15 mL of EtOAc and the organic solution was worked up in the usual manner giving 0.45 g of lid.

11e. A solution of 11d (0.45 g, 1.32 mmol) and ethyl acetimidate hydrochloride (0.2 g, 1.455 mmol) in 15 mL of ethanol was adjusted to pH 9–10 using a NaOH/ethanol solution. After stirring for 1 h at ambient temperature, the reaction was acidified to pH 2 with 5N HCl/dioxane. The reaction mixture was filtered from NaCl and concentrated in vacuum. The crude product (0.5 g) was purified using reverse phase separation, giving 0.225 g of 11e (40.91%). Anal. calcd. for C$_{22}$H$_{27}$N$_3$O$_3$.HCl.0.5 H$_2$O: C, 61.89; H, 6.85; N, 9.84; Cl, 8.30. Found: C, 61.68; H, 6.50; N, 9.88; Cl, 8.18.

11A,11B. Example 11e (.36 g, 0.86 mmol) was reduced under catalytic hydrogenation conditions using Pd black at 60 psi H$_2$ in 50% EtOH/AcOH solution for 24 h. The yield of the crude product was 0.35 g. After reverse phase separation two products were isolated: the faster running isomer (11A) 0.085 g and the slower running isomer 0.1 g (11B). Faster running isomer analysis: calcd. for $C_{14}H_{23}N_3O$, 1.5 HCl, 0.4AcOH, $2H_2O$: C, 48.82; H, 8.33; N, 11.54. Found: C, 48.56; H, 7.79; N, 11.95.

EXAMPLE 12

N-[5S-amino-6-oxo-6-(2-thienyl)hexyl] ethanimidamide, hydrate

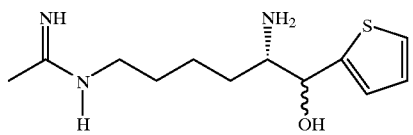

12

12a. 12a was prepared on a 2.84 mmol scale in the same manner as described for 11b using 11a and 2-thiophenelithium to yield 0.6 g (47.2%) of 12a after chromatography. Anal calcd. for: $C_{23}H_{30}N_2O_5S$: C, 61.86; H, 6.77; N, 6.27. Found: C, 61.53; H, 6.91; N, 6.12.

12b. 12b was prepared from 12a (0.6 g, 1.34 mmol) in the same manner as for 11c yielding 0.4 g (85.1%).

12c. 12c was prepared from 12b (0.4 g, 1.16 mmol) in the same manner as for 11e to yield 0.44 g of crude product.

12. To a solution of 12c (0.44 g; 1.14 mmol) and thioanisole (0.51 g, 0.44 mL, 2.28 mmol) in 10 mL of TFA at 0° C. trimethylsilyl trifluoromethanesulfonate (TMSOTf) (0.28 g, 0.27 mL, 2.28 mmol) is added. After mixing at same temperature for 1 h, $Et_2O$ is added. The crude 12 is filtered and is washed with $Et_2O$.

EXAMPLE 13

N-[5S-amino-6-hydroxy-6-(tetrahydrofuran-2-yl) hexyl]ethanimidamide

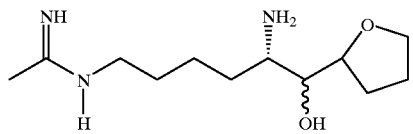

13

13. Example 13 was prepared in the same manner as example 11 on a 9.2 mmol scale starting with 2-bromofuran.

EXAMPLE 14

N-(5S-amino-6-oxoheptyl)ethanimidamide, dihydrochloride

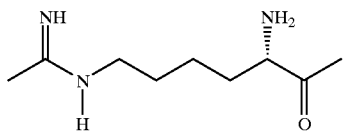

14

14a. To a stirring solution of 11a (1.0 g, 2.4 mmol) and N,N,N,N-tetramethylethylendiamine (0.96 g, 1.25 mL, 8.3 mmol) in 30 mL of dry THF at the −72° C. was added methyllithium, 1.4 M solution in $Et_2O$, (5.9 mL, 8.3 mmol). After stirring at same temperature for 3 h, the reaction mixture was added to 50 mL of 1M $KHSO_4$ solution and 50 mL of EtOAc at 0° C. The layers were separated, the organic layer was washed with 1×30 mL of brine and worked up in the usual manner giving 2.8 g of crude product which was purified using column chromatography. The yield of 14a was 0.9 g (55%).

14b. To example 14a (0.5 g, 1.2 mmol) in 10 mL of acetic acid was added 2 mL of 6N HCl/dioxane. The reaction was stirred for 20 min at ambient temperature then concentrated under vacuum. The residue was dissolved in $H_2O$ and lyophilized yielding 0.4 g (105%) of 14b.

14c. To a solution of 14b (0.4 g, 1.2 mmol) and TEA (0.56 mL, 3.9 mmol) in 10 mL of DMF was added methyl acetimidate hydrochloride (0.43 g, 3.9 mmol). After stirring for 16 h at ambient temperature, the reaction was filtered. The filtrate was concentrated under vacuum. The reaction mixture was partitioned between 15 mL 1N HCl and 20 mL DCM. The crude product from the aqueous HCl after stripping was purified using reverse phase separation, giving 0.26 g of 14c (60.5%).

14. 14c (0.26 g, 0.73 mmol) was reduced under catalytic hydrogenation conditions using Pd/C at 5 psi $H_2$ in 50% MeOH/HCl solution for 3 h. The yield of product was 0.18 g (94.7%). Analysis calcd. for $C_9H_{19}N_3O.2$ $HCl.H_2O$: C, 39.14; H, 8.39; N, 15.21. Found: C, 39.24; H, 8.32; N, 14.99.

EXAMPLE 15

N-(5S-amino-6,7-dihydroxy-6-methylheptyl) ethanimidamide, hydrochloride dihydrate

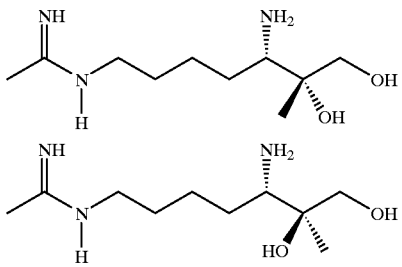

The absolute stereochemistry of the hydroxyl group at position C-6 has not been determined. The diastereomers have been separated as described below A difference in the biological activity between the diastereomers is seen.

15a. To a stirring suspension of methyltriphenylphosphonium bromide (6.21 g, 17.4 mmol) in 150 mL of toluene was added dropwise 0.5 M potassium hexamethyldisilazide in toluene (35.6 mL, 17.4 mmol). After stirring for 1.5 h, 14a (6.85 g, 17.4 mmol) in 50 mL of toluene was added to the stirring suspension cooled to −20 ° C. After 5 h, the reaction was warmed to 0° C., washed 2×100 mL of 1M $KHSO_4$, 1×100 mL of brine, dried, filtered, and concentrated in vacuo. The residue was purified by flash chromatography to yield 5.3 g (80%) of 15a, a white solid.

15b. To a stirring solution of 15a (3.3 g, 8.8 mmol) in 150 mL of acetone:$H_2O$ (3:1) was added N-methylmorpholine N-oxide (2.05 g, 17.5 mmol) and 2.5% $OsO_4$ in t-BuOH (9.5 mL, 0.9 mmol). After 18 h, 100 mL of $H_2O$, 25 g of celite, and 6 g $Na_2S_2O_4$ were added to the reaction. The reaction was filtered through a pad of wet celite. To the filtrate was added 180 mL of 1M $KHSO_4$. The filtrate was extracted with 3×250 mL EtOAc. The combined organic layers were dried, filtered, and stripped. The residue was purified by flash chromatography to yield 3.5 g (97%) of 15b.

15c. To a stirring solution of 15b (1.6 g, 3.9 mmol) in mL of HOAc was added 2.5 mL of 4N HCl/dioxane. After 30 min, solvent was removed under vacuum to quantitatively recover 15c.

15d. Example 15d was prepared in the same manner as described in example 14c starting with 15c (1.36 g, 3.9 mmol). The residue was applied to a reverse phase column (YMC AQ-363-10P, ODS) using a gradient of $CH_3CN$/ 0.025% HOAc. The first eluting isomer, 15d-1, weighed 0.11 g; the second eluting isomer, 15d-2 weighed 0.28 g; a mixture of the two weighed 0.18 g.

15A. Example 15A was prepared in the same manner as described for example 14 starting with 15d-1 (1.1 g, 2.6 mmol). After lyophilization, 0.82 g of 15A was recovered. Analysis calcd. for $C_{10}H_{23}N_3O_2 \cdot 2$ HCl·1.75 $H_2O$: C, 37.33; H, 8.93; N, 13.06. Found: C, 37.25; H, 8.70; N, 12.95.

15B. Example 15B was prepared in the same manner as described for example 14 starting with 15d-2 (0.28 g, mmol). After lyophilization, 0.21 g of 15B was recovered. Analysis calcd. for $C_{10}H_{23}N_3O_{2.2}$ HCl·2.2 $H_2O$: C, 36.41; H, 8.98; N, 12.74. Found: C, 36.31; H, 8.97; N, 12.34.

EXAMPLE 16

N-(5S-amino-6,7-dihydroxyoctyl) ethanimidamide, dihydrochloride hydrate

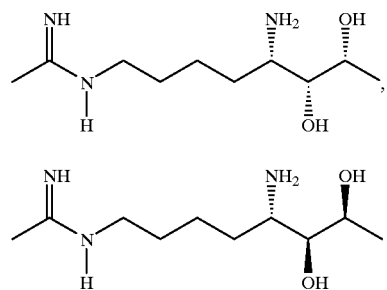

16A, 16B. Example 16A and 16B were prepared in the same manner as described for examples 3A and 3B starting with 3b and ethyltriphenylphosphonium bromide. 16B: Analysis calcd. for $C_{10}H_{23}N_3O_2 \cdot 2$ HCl·1.8 $H_2O$: C, 37.22; H, 8.93; N, 13.02. Found: C, 37.47; H, 9.05; N, 12.93.

EXAMPLE 17

4S-amino-2,3-dihydroxy-8-[(1-iminoethyl)amino] octanoic acid

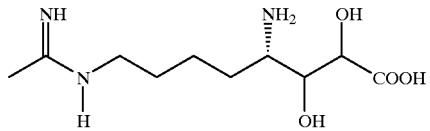

17a. Example 17a is prepared starting with 3b and (carbomethoxymethyl)triphenylphosphonium bromide.

17b. To a stirring solution of 17a (3.3 mmol) in 80 mL of acetone:$H_2O$ (3:1) is added N-methylmorpholine N-oxide (0.64 g, 4.8 mmol) and 2.5% $OsO_4$ in t-BuOH (3.4 mL, 0.34 mmol). After 18 h, 120 mL of $H_2O$, 8 g of celite, and 1.6 g $Na_2S_2O_4$ are added to the reaction. The reaction is filtered through a pad of wet celite. To the filtrate is added 200 mL of 1M $KHSO_4$. The filtrate is extracted with 3×200 mL EtOAc. The combined organic layers are dried, filtered, and stripped.

17c. Benzyloxycarbonyl protecting group is removed from 17b by catalytic hydrogenation using Pd black as the catalyst yielding 17c quantitatively.

17d. To a stirring solution of 17c (14.9 mmol) and TEA (3.3 mL, 24 mmol) in 10 mL of DMF is added methyl acetimidate (2.44 g, 22.2 mmol). After 16 h, TEA.HCl is filtered from the reaction and is washed with a minimum of DMF. The filtrate is adjusted to pH 3 with 1N HCl. The filtrate is concentrated under high vacuum. The residue is applied to a reverse phase column (YMC AQ-363-10P, ODS) using a gradient of 20% $CH_3CN$/0.025% HOAc to 50% $CH_3CN$/ 0.025% HOAc.

17e Example 17d is treated with 1N HCl for 1 h at ambient temperature. The aqueous solution is lyophilized to give 17e.

17. 17d dissolved in 20 mL 2N HCl is refluxed for 60 min. The reaction is diluted with $H_2O$ and lyophilized.

EXAMPLE 18

N-(6,7-diacetyloxy-5S-aminoheptyl) ethanimidamide, hydrochloride monohydrate

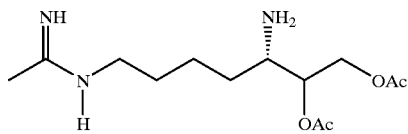

18a To a stirring solution of 3e (0.90 g, 2.3 mmol) and DMAP (0.61 g, 5.0 mmol) in DCM was added acetic anhydride (2.1 mL, 23 mmol). After 18 h, solvent was removed under vacuum. The residue was taken up in 50 mL EtOAc which was washed with 3×50 mL satd $KHCO_3$ solution, 1×50 mL 1M $KHSO_4$, and 1×50 mL $H_2O$. The organic layer was dried over $Na_2SO_4$ anhydrous, filtered, and stripped to yield 0.99 g (89%) of 18a, a pale yellow glass. Anal calcd for $C_{24}H_{36}N_2O_8 \cdot 0.2$ $H_2O$: C, 59.54; H, 7.58; N, 5.79. Found: C, 59.75; H, 8.42; N, 6.77.

18b Example 18b (0.90 g, 1.9 mmol) was prepared in same manner as 3f to yield 0.64 g (1.8 mmol) of 18b.

18c. To a stirring solution of 18b (0.64 g, 1.8 mmol) in 10 mL of DMF was added a 2 mL solution of methyl acetimidate (0.10 g, 0.9 mmol) which had been neutralized with TEA (0.12 mL, 0.9 mmol) and filtered through glass wool to remove TEA.HCl. This was repeated 4× over two hours. After stirring an additional 2 h, the reaction was adjusted to pH 3 with 1N HCl. After solvent was removed under vacuum, the crude product was purified by reverse phase chromatography. Not only was desired product 18c (0.38 g, 51%) obtained but also the monoacetoxy compound, 19a (0.11 g).

18. Example 18 was prepared from 18c (0.38 g, 0.9 mmol) dissolved in 2 mL HOAc to which was added 1 mL 4N HCl/dioxane. The solvent was removed under vacuum. The residue was dissolved in $H_2O$ and lyophilized to give 18 (0.26 g, 81%). Analysis calcd. for $C_{13}H_{25}N_3O_4 \cdot 1.75$ HCl·1 $H_2O$: C, 42.29; H, 7.85; N, 11.38. Found: C, 42.41; H, 7.57; N, 10.68.

EXAMPLE 19

N-(5S-amino-6-hydroxy-7-acetoxyheptyl)
ethanimidamide, hydrochloride monohydrate

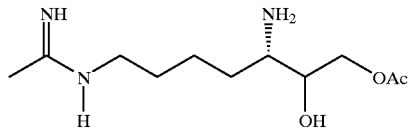

19. Example 19a (0.11 g, 0.29 mmol) was dissolved in 1 mL of HOAc. (see example 18c for isolation of 19a) To the above solution was added 1 mL of 4N HCl/dioxane. After 5 min, the solvent was removed under vacuum and the residue taken up in $H_2O$ and lyophilized. Analysis calcd. for $C_{11}H_{23}N_3O_3 \cdot 2$ HCl$\cdot 1.2$ $H_2O$: C,38.87; H, 8.13; N, 12.36. Found: C, 38.81; H, 8.01; N, 12.07.

EXAMPLE 20

N-(5S-amino-6,7,8-trihydroxyoctyl)ethanimidamide

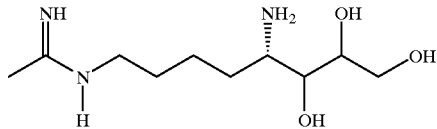

20a. 17b dissolved in THF is treated with $LiBH_4$ to remove the benzoxycarbonyl group and reduce the ester to the alcohol.

20b To a stirring solution of 20a (14.9 mmol) and TEA (3.3 mL, 24 mmol) in 10 mL of DMF is added methyl acetimidate (2.44 g, 22.2 mmol). After 16 h, TEA.HCl is filtered from the reaction and is washed with a minimum of DMF. The filtrate is adjusted to pH 3 with 1N HCl. The filtrate is concentrated under high vacuum. The crude product is purified by reverse phase chromatography 20 Example 20b is treated with 1N HCl for 1 h at ambient temperature. The aqueous solution is lyophilized to give 20.

EXAMPLE 21

N-(5S-amino-7,8-dihydroxyoctyl)ethanimidamide

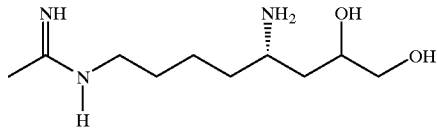

21. Example 21 is prepared in the same manner as 3A, 3B starting with 1b.

EXAMPLE 22

N-[5S-amino-5-(4-methyl-2-oxo-1,3-dioxolan-4-yl)
pentyl]ethanimidamide

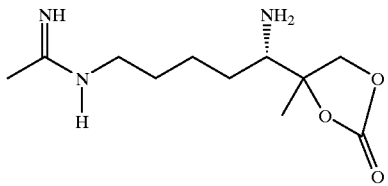

22. 15b is treated with phosgene to generate cyclic carbonate. Example 22 is synthesized by methods described in example 15.

EXAMPLE 23

N-(5S-amino-6-hydroxy-7-methoxyheptyl)
ethanimidamide

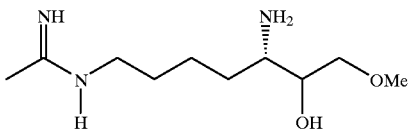

23a. To a stirring solution of 3d (3.62 g, 10 mmol) in 25 mL of DCM was added m-chloroperbenzoic acid (2.59 g, 15 mmol). After 16 h, solvent was removed under vacuum. The resulting residue was taken up in 100 mL of EtOAc and washed with 3×100 mL satd $KHCO_3$ solution. The organic layer was dried, filtered, and stripped. The crude product was purified by flash column chromatography to give 2.89 g (76%) of 23a.

23b. Example 23b is prepared in the manner described in *Tetrahedron Lett,* 1994, 35, 8977–80. To a stirring suspension of NaOMe in 15 mL of toluene-THF (2:1) cooled to −78° C. is added $Et_2AlCl$ (3.6 mL, 3.6 mmol [1M solution]). After 30 min, 10 mL toluene solution of 23a (0.63 g, 1.7 mmol) is added dropwise to NaOMe suspension. The reaction is quenched after 1.5 h with $Na_2SO_4 \cdot 10$ $H_2O$ (5 g) and $Na_2CO_3$ (0.3 g). After removing the ice bath, the suspension is stirred for 1 h. The salts are filtered from reaction and the filtrate is concentrated to yield 23b.

23. Example 23 is prepared from 23b in the same manner as described in examples 3f and 3.

EXAMPLE 24

N-[5S-amino-6-hydroxy-7-(ethylthio)heptyl]
ethanimidamide

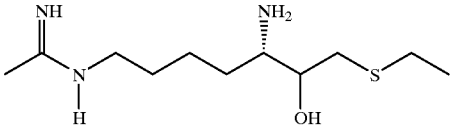

24a. To stirring ethanethiol (0.19 mL, 2.5 mmol) was added tetra-n-butylammonium fluoride. After 15 min, 23a (0.79 g, 2.1 mmol) in 15 mL $CH_3CN$ was added. After 16 h, the solvent was removed. The crude product is purified by flash chromatography.

24b. Example 24a is treated with $LiAlH_4$ to remove the benzyloxycarbonyl protecting group.

24. Example 24 is prepared from 24b using conditions described in example 3.

EXAMPLE 25

N-[5S-amino-6-hydroxy-7-(methylsulfinyl)heptyl] ethanimidamide

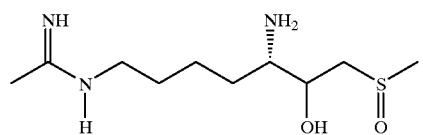

25. Example 25 is prepared from 24 by treatment with 30% $H_2O_2$ and acetic acid at room temperature for 1 h.

EXAMPLE 26

N-[5S-amino-6-hydroxy-7-(methylsulfonyl)heptyl] ethanimidamide

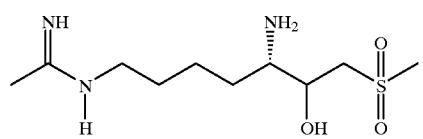

26. Example 26 is prepared from 24 by treatment with 30% $H_2O_2$ and acetic acid at 60° C. for 4 h.

EXAMPLE 27

N-[5S-amino-6-hydroxy-7-[(phenylmethyl)thio] heptyl]ethanimidamide

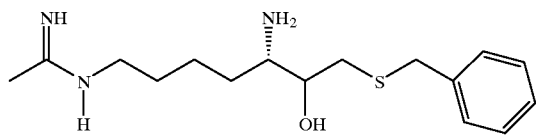

27. Example 27 is prepared from 23a and benzyl mercaptan in the same manner as 24.

EXAMPLE 28

N-[5S-amino-6-hydroxy-7-[(phenylmethyl)sulfinyl] heptyl]ethanimidamide

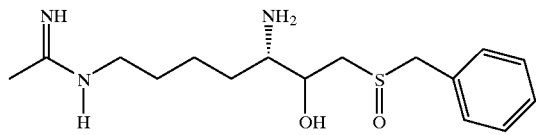

28. Example 28 is prepared in the same manner as 25 starting with 27.

EXAMPLE 29

N-[5S-amino-6-hydroxy-7-[(phenylmethyl)sulfonyl] heptyl]ethanimidamide

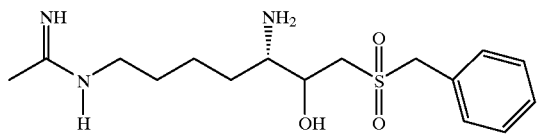

29. Example 29 is prepared in the same manner as 26 starting with 27.

EXAMPLE 30

4S-amino-2,2-difluoro-3-hydroxy-8-[(1-iminoethyl) amino]-3-methyloctanoic acid

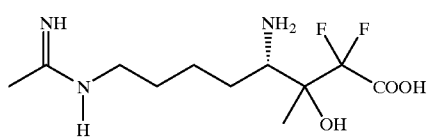

30a. To a refluxing suspension of Zn (2 mg-atm) and ethyl bromodifluoroacetate (2 mmol) in 10 mL is added dropwise a solution of 14a (1 mmol) in 2 mL of THF. After 1 h, the reaction is cooled to room temperature. To the reaction is added 20 mL of EtOAc and 20 mL 1M $KHSO_4$. The layers are separated and the organic layer is treated in the normal manner to yield 30a.

30b. Conditions described in example 14 are used to prepare 30b from 30a.

30. To remove the ethyl ester from 30b, conditions described in example 1 are used.

EXAMPLE 31

N-(5S-amino-6-fluoro-7-hydroxy-6-methylheptyl) ethanimidamide

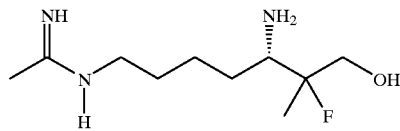

31a. To a stirring solution of 15b (1.5 mmol) in 10 mL of pyridine is added $Ph_3CCl$ (1.5 mmol). After 16 h, the reaction is concentrated under vacuum. The residue is taken up in 20 mL of EtOAc and is washed with 3×20 mL 1M $KHSO_4$, 2×20 mL saturated $KHCO_3$, and 1×20 mL brine. The organic layer is treated in the normal manner to obtain 31a.

31b. To a stirring solution of 31a in dioxane is added $Et_2NSF_3$. After 40 h, the reaction is concentrated under vacuum and chromatographed to obtain 31b.

31. Using methodology described for example 15, example 31 is synthesized from 31b.

EXAMPLE 32

N-[5S-amino-6,7-dihydroxy-7-(2-thienyl)heptyl]ethanimidamide, dihydrochloride

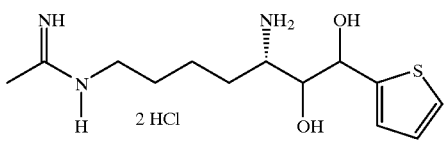

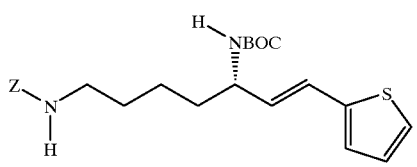

32. A mixture of palladium acetate (Johnson Matthey, 0.29 mmol), tri-o-tolylphosphine (0.6 mmol), 2-bromothiophene (16.0 mmol), and triethylamine (16 mmol) is refluxed under nitrogen for 30 min. The mixture is cooled to room temperature, and 3d (14.4 mmol) in 6 mL of acetonitrile is added. The reaction is refluxed for 24 h, cooled to room temperature, and stripped of all solvent under reduced pressure. The residue is partitioned between sat. NaHCO$_3$ and EtOAc and the organic phase is dried (MgSO$_4$), filtered, and stripped. The residue is chromatographed on silica gel to give 32a.

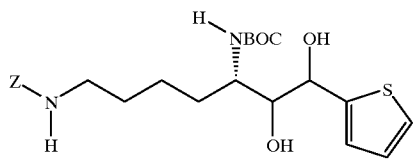

32b. Osmium tetroxide is reacted with 32a by the method used in the preparation of 3e, to yield 32b.

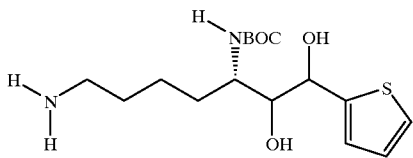

32c. A solution of 32b in AcOH is treated with H$_2$ (5 psi) over Pd black for 20 h. The reaction mixture is assessed by thin layer chromatography to find the extent of reaction. If necessary, fresh Pd black is added and the reaction continued. This process is repeated until the reaction is completed. The reaction mixture is filtered and concentrated in vacuo to yield 32c.

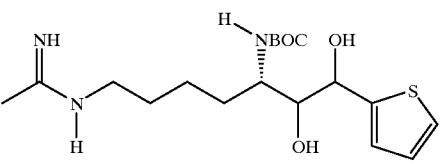

32d. An equimolar solution of 32c and ethyl acetimidate hydrochloride in EtOH is stirred for 18 h. The reaction solution is concentrated in vacuo to yield a white foam. This material is purified by reversed phase HPLC to yield 32d.

32. To a stirred solution of 32d in AcOH (glacial) is added HCl (6.95 M in dioxane). The resulting solution is stirred for 2 h. The solution is concentrated in vacuo and triturated with diethyl ether to yield 32.

EXAMPLE 33

N-[5S-amino-6,7-dihydroxy-7-(1H-imidazol-5-yl)heptyl]ethanimidamide, trihydrochloride

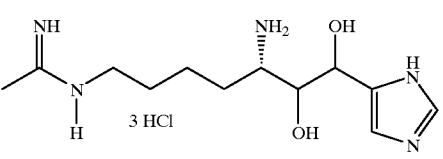

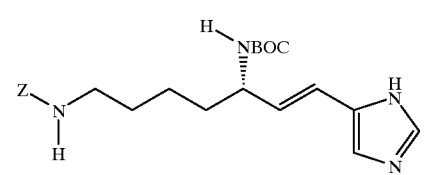

33a. 4-Bromoimidazole (K&K Laboratories) is treated as described in the preparation of 32a, replacing the 2-bromothiophene in that preparation. The product is 33a.

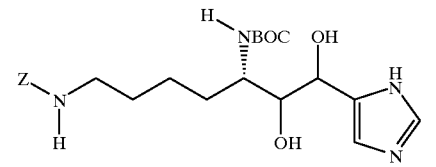

33b. By the method of Example 3e, osmium tetroxide is reacted with 33a to yield 33b.

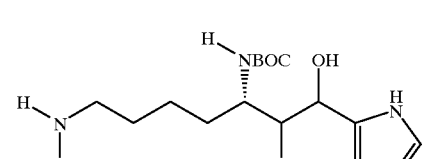

33c. A solution of 33b in AcOH is treated with H$_2$ (5 psi) over Pd black for 20 h. The reaction mixture is filtered and concentrated in vacuo to yield 33c.

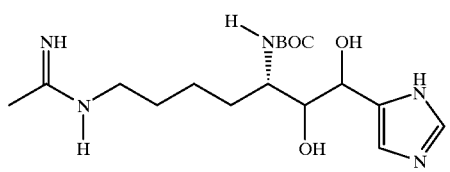

33d

33d. An equimolar solution of 33c and ethyl acetimidate hydrochloride in EtOH is stirred for 18 h. The reaction solution is concentrated in vacuo to yield a white foam. This material is purified by reversed phase HPLC to yield 33d.

33. To a stirred solution of 33d in AcOH (glacial) is added HCl (6.95 M in dioxane). The resulting solution is stirred for 2 h. The solution is concentrated in vacuo and triturated with diethyl ether to yield 33.

EXAMPLE 34

N-[5S-amino-5-(2,2-dimethyl-1,3-dioxolan-4-yl)pentyl]ethanimidamide, dihydrochloride

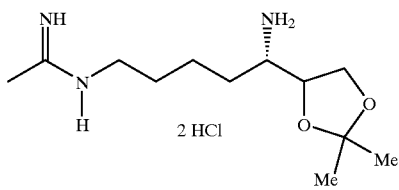

34

34. 3B (10 mmol) is dissolved in DMF and 2,2-dimethoxypropane (20 mmol) is added, as is 6N HCl in dioxane (2 mmol). The mixture is protected from moisture and stirred overnight. It is then stripped to a residue in a rotary evaporator using an oil pump as a vacuum source. The residue is suspended in dry acetone, stirred for 30 min, and stripped again. The resulting residue is dissolved in cold water, shelled, and lyophilized to give 34.

EXAMPLE 35

N-[5S-amino-5-(2-phenyl-1,3-dioxolan-4-yl)pentyl]ethanimidamide, di(4-methylbenzenesulfonate)

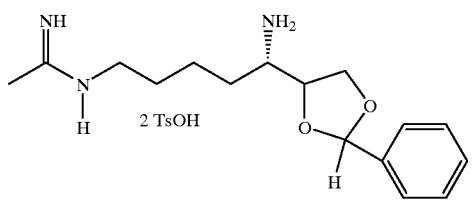

35

35. 3B (27.7 mmol), 1,1,1-trichloroethane (350 mL), benzaldehyde (55.4 mmol), and toluensulfonic acid monohydrate (55.4 mmol) are placed in a 500 mL round bottom single neck flask fitted with a Soxhlet extractor whose thimble is filled with 5A molecular sieves (8–12 mesh beads). The flask is immersed in an oil bath (bath temperature 120° C.) and the mixture is refluxed with vigorous stirring for 16 h. The reaction is then cooled and the mixture is stripped to a residue in a rotary evaporator using an oil pump as a vacuum source. The residue is dissolved in cold water, shelled, and lyophilized to give 35.

EXAMPLE 36 methyl 2-[[3S-amino-2-hydroxy-7-[(1-iminoethyl)amino]heptyl]oxy]propanoate, dihydrochloride

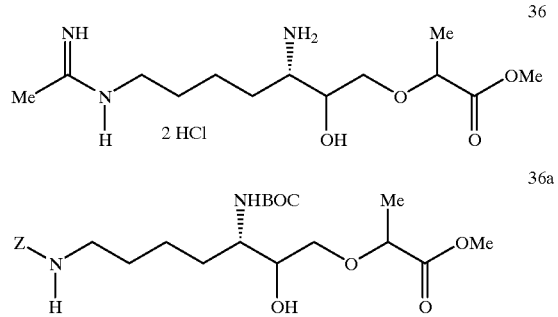

36a. Sodium hydride (50% in mineral oil, 10.5 mmol) is washed twice with hexane and suspended in DMF. Methyl lactate (10 mmol) is dissolved in DMF and added carefully to the NaH suspension with stirring. The mixture is stirred for 30 min, and a solution of 23a (9 mmol) and anhydrous zinc chloride (9 mmol) in THF is added. This mixture is immersed in a 60° C. oil bath and stirred overnight. It is then worked up to give 36a.

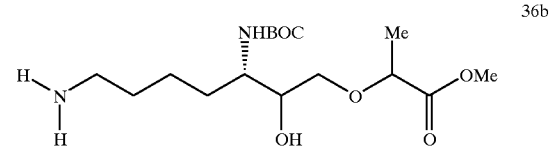

36b

36b. A solution of 36a in AcOH is treated with $H_2$ (5 psi) over Pd black for 20 h. The reaction mixture is filtered and concentrated in vacuo to yield 36b.

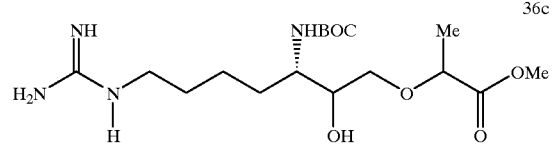

36c

36c. An equimolar solution of 36b and ethyl acetimidate hydrochloride in EtOH is stirred for 18 h. The reaction solution is concentrated in vacuo to yield a white foam. This material is purified by reversed phase HPLC to yield 36c.

36. To a stirred solution of 36c in AcOH (glacial) is added HCl (6.95 M in dioxane). The resulting solution is stirred for 2 h. The solution is concentrated in vacuo and triturated with diethyl ether to yield 36.

EXAMPLE 37

N-[5S-amino-5-(2-methyl-3-oxo-1,4-dioxan-5-yl)pentyl]ethanimidamide, dihydrochloride

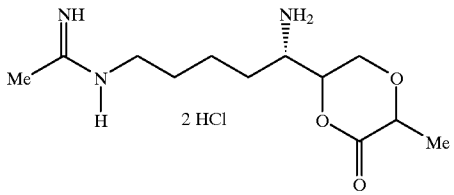

37. A solution of 36 in 1 M aqueous HCl is refluxed for two hours. The reaction is stripped to small volume, shelled, and lyophilized to give the title compound.

EXAMPLE 38

N-[5S-amino-6-hydroxy-7-(2-hydroxyphenyl)heptyl]ethanimidamide, dihydrochloride

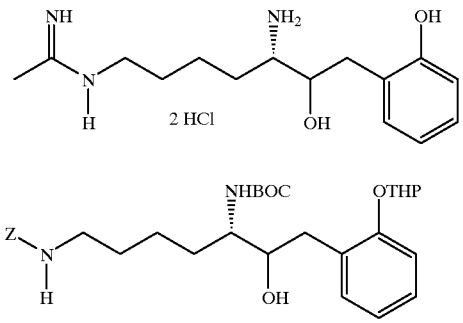

38a. 2-(Tetrahydropyran-2-yloxy)phenyllithium is prepared from 2-(tetrahydropyran-2-yloxy)phenyl bromide and n-BuLi in THF at −78° C. It is then reacted with 23a in THF at −78° C., allowing the temperature to rise to ambient temperature. The reaction mixture is worked up in the usual way to yield 38a.

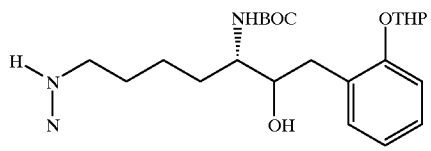

38b. A solution of 38a in AcOH is treated with H$_2$ (5 psi) over Pd black for 20 h, The reaction mixture is filtered and concentrated in vacuo to yield 38b.

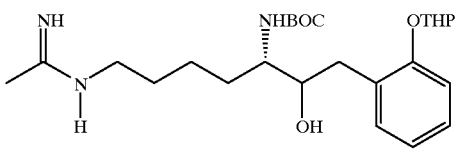

38c. An equimolar solution of 38b and ethyl acetimidate hydrochloride in EtOU is stirred for 18 h. The reaction solution is concentrated in vacuo to yield a white foam, This material is purified by reversed phase HPLC to yield 38c.

38. To a stirred solution of 38c in AcOH (glacial) is added HCl (6.95 M in dioxane). The resulting solution is stirred for 2 h. The solution is concentrated in vacuo and triturated with diethyl ether to yield 38.

EXAMPLE 39

N-[5S-amino-7,7,7-trifluoro-6-hydroxy-6-methylheptyl)ethanimidamide

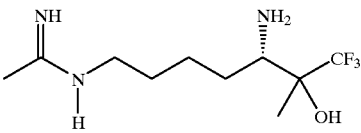

39a. To a stirring solution of CF$_3$I (10 mmol) in 5 mL of DMF at −40° C. is added Zn (10 mg-atm) and 14a (0.5 mmol) in 10 mL of DMF. After stirring for 1 h at −20° C., the reaction is warmed to room temperature and partitioned between H$_2$O and EtOAc. The organic layer is worked up in the usual manner to obtain desired trifluoromethyl alcohol.
39. Using conditions described in example 3, the desired compound is obtained.

EXAMPLE 40

N-(5S-amino-6-hydroxyheptyl)ethanimidamide, dihydrochloride dihydrate

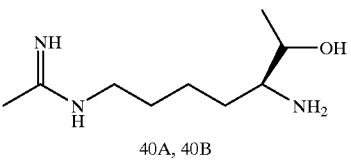

40A, 40B

40a. To a 50 mL solution of 14a (1.5 g, 4.0 mmol) in EtOH was added NaBH$_4$. After 2 h, the reaction was concentrated under vacuum. The residue was taken up in 50 mL of EtOAc and 30 mL of H$_2$O. The organic was treated in the usual manner to obtain 1.5 g of 40a.

40A,40B. Examples 40A, 40B were prepared in same manner as described in example 15. The first eluting fractions from the final purification by reverse phase chromatography were a single isomer (40A). The second eluting fractions were a mixture of two isomers (40B). 40A Analysis calcd. for C$_9$H$_{21}$N$_3$O.2 HCl.2 H$_2$O: C, 36.49; H, 9.19; N, 14.18. Found: C, 36.73; H, 8.93; N, 14.13. 40B Analysis calcd. for C$_9$H$_{21}$N$_3$O.3 HCl.2 H$_2$O: C, 32.49; H, 8.48; N, 12.63. Found: C, 32.37; H, 8.08; N, 12.04.

EXAMPLE 41

N-[5S-amino-5-(1H-tetrazol-5-yl) pentyl] ethanimidamide, dihydrochloride

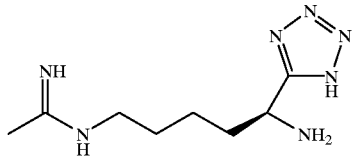

41a. To a stirring solution of N-α-Boc-N-ε-Z-L-Lys. (3.8 g, 10 mmol), 2-aminopropionitrile fumarate (1.9 g, 10 mmol), 1-hydroxybenzotriazole hydrate (4.4 g, 10 mmol), and NMM (3.3 mL, 30 mmol) in 50 mL of DMF cooled in an ice bath was added (1H-1,2,3-benzotriazol-1-yloxy)-tris(dimethylamino)phosphonium hexafluorophosphate (BOP) (4.4 g, 10 mmol). After stirring 18 h at ambient temperature, the filtrate was concentrated under vacuum. The residue was distributed between 100 mL of EtOAc and 50 mL of 1M KHSO₄ solution. The layers were separated. The organic layer was washed with 1×50 mL of saturated KHCO₃ solution and 1×50 mL of brine and was worked up in the usual manner giving 3.9 g of 41a.

41b. To a stirring solution of 41a (3.9 g, 9 mmol) in 90 mL of THF was added PPh₃, DEAD, TMSN₃. After 24 h of stirring at ambient temperature, the reaction was cooled to 0° C. to which was added slowly 300 mL of 6% Ce (NH₄)₂(NO₃)₆. Additional Ce(NH₄)₂(NO₃)₆ was added until evolution of N₂ ceased. The layers were separated and the aqueous layer was extracted 2×250 mL of DCM. The combined organic layers were treated in the usual manner to yield 3.1 g of 41b.

41c. To a stirring solution of 41b (2.7 g, 5.9 mmol) in 60 mL of THF was added 7 mL of 1N NaOH. After 18 h, the reaction was concentrated under vacuum. The residue was taken up in 50 mL of EtOAC and 50 mL of 0.5N NaOH. The layers were separated and the aqueous layer was washed 2×50 mL of EtOAc. The aqueous layer was acidified to pH 3 and extracted 3×40 mL EtOAc. The second organic extractions were worked up in the usual manner to obtain 0.3 g of 41c. The original organic extracts were worked up in the usual manner and they also contained product (2 g).

41. To obtain example 41, conditions described in example 3 were used.

EXAMPLE 42

(A) methyl 3S-amino-2S-hydroxy-7-[(1-iminoethyl)amino]heptanoate (B) methyl 3S-amino-2R-hydroxy-7-[(1-iminoethyl)amino]heptanoate

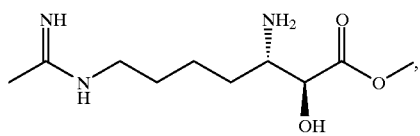

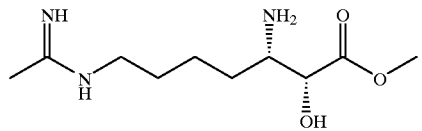

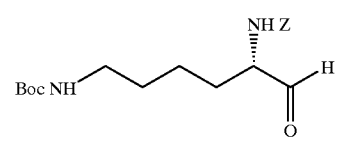

42a. To a stirring solution of N-α-Z-N-α-Boc-L-Lys-N(OMe)Me 11a in ether at 0° C. is added LiAlH₄ (1.2 equiv.) in portions. The resulting solution is stirred for 1 h at 0° C., then carefully quenched with KHSO₄ (1 M). The layers are separated and the aqueous extracted with ether. The combined organic solutions are extracted with KHSO₄ (1 M) and NaHCO₃ (satd.) dried (Na₂SO₄) and evaporated to yield the aldehyde 42a, which is used directly in the next step.

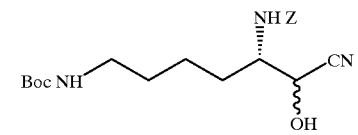

42b. A stirred mixture of the aldehyde 42a in EtOAc and KCN (1 equiv.) in water, at 0° C., is treated with an aqueous solution of NaHS₃ (satd.). The solution is stirred for 1 h, and the layers separated. The organic solution is dried over Na₂SO₄ anhydrous and concentrated to yield the resulting cyanohydrin 42b.

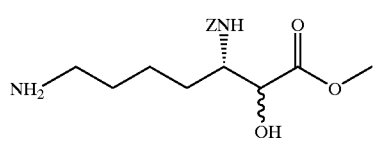

42c. The cyanohydrin 42b is treated with methanolic/HCl to yield the methyl ester 42c.

42A,42B. The amine 42c is treated with methyl acetimdate according to the procedure for 11e. The product is then treated with Pd black according to the procedure for 11, and the isomers separated on reversed phase HPLC to yield 42A and 42B.

EXAMPLE 43

(A) 3S-amino-2S-hydroxy-7-[(1-iminoethyl)amino]heptanoic acid (B) 3S-amino-2R-hydroxy-7-[(1-iminoethyl)amino]heptanoic acid

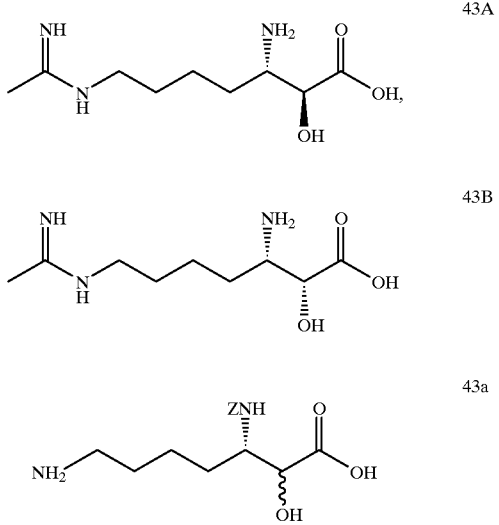

43a. The cyanohydrin 42b is treated with concentrated HCl at 0° C. for 12 h. The solution is concentrated under vacuum and the ammonium chloride is removed by filtration. The residue is then dried to yield the hydroxy acid 43a.

43A,43B. The amine 43a is treated with methyl acetimidate according to the procedure for 11e. The product is then treated with Pd black according to the procedure for 11, and the isomers separated on reversed phase HPLC to yield 43A and 43B.

EXAMPLE 44 methyl 3S-amino-7-[(1-iminoethyl)amino]-2-oxoheptanoate

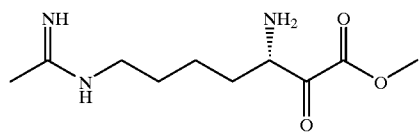

44. A solution of 42A and 42B in water is treated with $MnO_2$. The solution is filtered and concentrated to yield 44.

EXAMPLE 45 methyl 3-amino-4-[3-[(aminoiminomethyl)amino]phenyl]butanoate

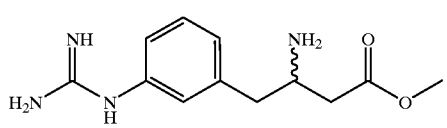

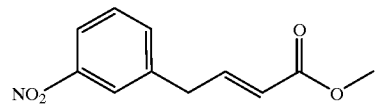

45a. To a stirred solution of oxalyl chloride (1.1 equiv.) in dry $CH_2Cl_2$ is slowly added at −60° C. a solution of dry DMSO in $CH_2Cl_2$. After the solution is stirred for 5 min a solution of 3-nitrophenethyl alcohol (1 equiv.) in dry $CH_2Cl_2$ is added. The solution is stirred for an additional 15 min and subsequently TEA is added. After stirring for 5 min the cooling bath is removed and the solution is allowed to reach room temperature. The reaction is quenched with water. The organic layer is removed and the aqueous layer extracted with additional $CH_2Cl_2$. The combined organic extracts are washed with brine and water, dried($Na_2SO_4$) and evaporated to yield the aldehyde. The aldehyde is treated with carbomethoxymethyl)triphenylphosphonium bromide by the method of 17a, to yield the ester 45a.

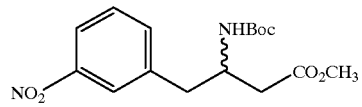

45b. A solution of 45a and ammonium chloride (3 equiv.) in glacial acetic acid is refluxed for 3 h. The solvent is removed in vacuo and the residue is partitioned between EtOAc and aqueous $Na_2CO_3$. The layers are separated and the organic phase is dried ($Na_2SO_4$) and evaporated to yield the amine. The residue is taken up in THF and treated with di-t-butyl dicarbonate (1.5 equiv.) and triethylamine (1.1 equiv.). The resulting solution is refluxed for 2 h, concentrated in vacuo and purified by flash column chromatography to yield 45b.

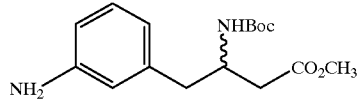

45c. A solution of 45b in methanol is hydrogenated in the presence of 10% Pd/C to yield 45c.

45. Aminoiminomethanesulphonic acid (1.1 equiv.) is added to a solution of 45c in methanol. The solution is stirred for 24 h. The solvent is removed and the residue is dissolved in water. The pH is adjusted to greater than 7 with NaOH. The mixture is extracted with EtOAc, dried ($Na_2SO_4$) and concentrated in vacuo. The residue is the treated with methanol/HCl to yield 45.

EXAMPLE 46

3-amino-4-[3-[(aminoiminomethyl)amino]phenyl]butanoic acid

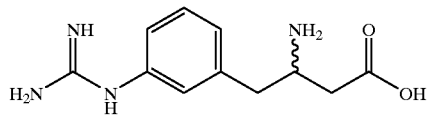

46. 45 is dissolved in 2N HCl and refluxed for 1 h. The reaction is diluted with water and lyophilized to yield 46.

EXAMPLE 47

N-[5S-amino-6-hydroxy-6-(2-hydroxyphenyl)hexyl]ethanimidamide

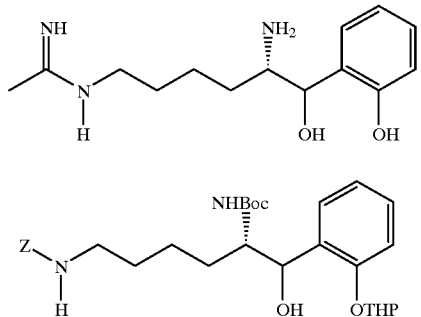

47a. 2-(Tetrahydropyran-2-yloxy)phenyllithium is prepared from 2-(tetrahydropyran-2-yloxy)phenyl bromide and n-BuLi in THF at −78° C. It is then reacted with 3b in THF at −78° C., allowing the temperature to rise to ambient temperature. The reaction mixture is worked up in the usual way to yield 47a.

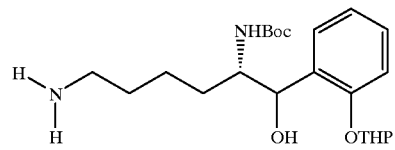

47b. A solution of 47a in ACOH is treated with $H_2$ (5 psi) over Pd black for 20 h. The reaction mixture is filtered and concentrated in vacuo to yield 47b.

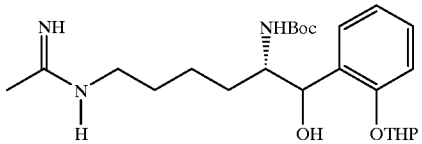

47c. An equimolar solution of 47b and ethyl acetimidate hydrochloride in EtOH is stirred for 18 h. The reaction solution is concentrated in vacuo to yield a white foam. This material is purified by reversed phase HPLC to yield 47c.
47. To a stirred solution of 47c in AcOH (glacial) is added HCl (6.95 M in dioxane). The resulting solution is stirred for 2 h. The solution is concentrated in vacuo and triturated with diethyl ether to yield 47.

EXAMPLE 48

N-(5S-amino-6-hydroxyhexyl)ethanimidamide

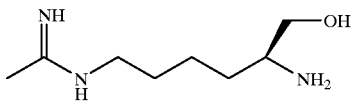

48. Example 48 was prepared using methods described in example 3 starting with 3c. h.r.m.s. $C_8H_{19}N_3O$: 174.16.

EXAMPLE 49

N-[5-amino-5-(5-methyloxazol-2-yl)pentyl]ethanimidamide, hydrochloride hydrate

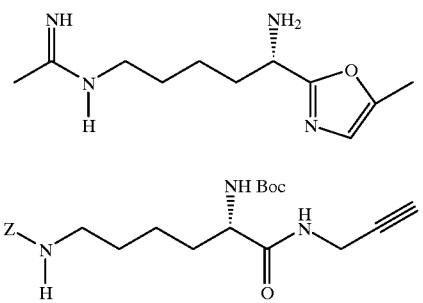

To a cooled (0° C.) solution of N-α-Boc-N-ε-Z-Lys (3.8 g, 10 mmol), propargylamine (550 mg, 10 mmol) and $Et_3N$ (1 g, 10 mmol) in DMF was added HOBT (1.35 g, 10 mmol) and EDC (1.92 g, 10 mmol). The solution was allowed to gradually warm to RT over 16 h. EtOAc (500 mL) was added to the reaction solution followed by extraction with brine (4×100 mL), dried ($Na_2SO_4$) and concentrated to yield an oil. The product was crystallized from ether/hexane to yield 49a (4.3 g) as a white solid. Anal. Calcd for $C_{22}H_{31}N_3O_2$: C, 63.29; H, 7.48; N,10.06. Found: C, 63.04; H, 7.41;

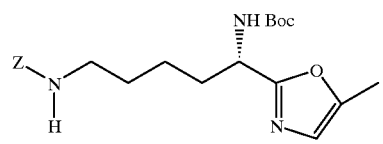

A solution of 49a (1.8 g, 4.3 mmol) and mercuric acetate (240 mg, .8 mmol) in AcOH (80 mL) was refluxed for 2 h. The solution was stirred at RT for 2 h. The solvent was removed and the residue taken up in $CHCl_3$ (250 mL) and washed with NaOH (1M, 1×100 mL) and brine (100 mL), dried ($Na_2SO_4$) and evaporated to yield an oil. The product was purified by flash chromatography to yield 49b. Anal. Calcd for $C_{22}H_{31}N_3O_2 \cdot 2\ H_2O$: C, 62.75; H, 7.52; N,9.98. Found: C, 62.40; H, 7.40; N. 9.61.

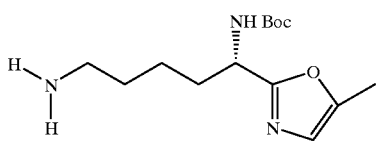

A solution of 49b (2.0 g, 4.75 mmol) in ethanol was treated with $H_2$ (5 psi) over Pd/C (10%) for 3 h. The reaction mixture was filtered and concentrated in vacuo to yield 49c.

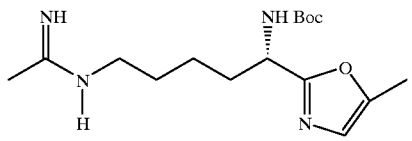

An equimolar solution of 49c (1.0 g, 3.5 mmol)and ethyl acetimidate hydrochloride in EtOH was stirred for 18 h. The reaction solution is concentrated in vacuo to yield a white foam (1.2 g).
49. To a stirred solution of 49d (1.2 g, 3.3 mmol) in AcOH (glacial, 25 mL) was added HCl (5.8 M in dioxane, 3 mL). The resulting solution was stirred for 1 h. The solution is concentrated in vacuo and purified by reversed phase HPLC to yield 49. Anal. Calcd for $C_{11}H_{20}N_4O.2.1$ HCl.1.6 $H_2O$: C: 40.07; H: 7.74; N:16.99; Cl:22.58. Found: C: 40.33; H: 8.00; N: 16.68, Cl: 22.75.

EXAMPLE 50

2S-amino-N-hydroxy-6-[(1-iminoethyl)amino] hexanamide, hydrochloride

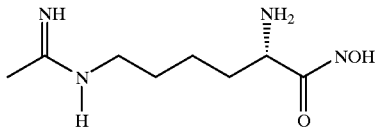

50a. Starting with N-α-Z-N-ε-Boc-Lys and O-benzylhydroxylamine hydrochloride example 50 was synthesized using conditions described in examples 11a, 11c–e, 11. Anal. Calcd for $C_8H_{18}N_4O_2.1.5$ HCl.0.25 HOAc .$H_2O$: C: 35.21; H: 7.82; N:19.32. Found: C: 35.32; H: 7.81; N: 19.75.

Biological Data

The activity of the above listed compounds as NO synthase inhibitors has been determined in the following assays:

Citrulline Assay for Nitric Oxide Synthase

Nitric oxide synthase activity was measured by monitoring the conversion of L-[2,3-3H]-arginine to L-[2,3-3H]-citrulline (1,2). Human inducible NOS (hiNOS), human endothelial constitutive NOS (hecNOS) and human neuronal constitutive NOS (hncNOS) were each cloned from RNA extracted from human tissue. The recombinant enzymes were expressed in insect cells using a baculovirus vector. Enzyme activity was isolated from cell extracts and partially purified by DEAE-Sepharose chromatography (2). Mouse inducible NOS (miNOS) was prepared from an extract of LPS-treated mouse RAW 264.7 cells and rat brain constitutive NOS (rcNOS) was prepared from an extract of rat cerebellum. Both preparations were partially purified by DEAE-Sepharose chromatography (2). Enzyme and inhibitors were added to give a volume of 50 μL in 50 mM Tris (pH 7.6) and the reaction initiated by the addition of 50 μL of a solution containing 50 mM Tris (pH 7.6), 2.0 mg/mL bovine serum albumin, 2.0 mM DTT, 4.0 mM $CaCl_2$, 20 μM FAD, 100 μM tetrahydrobiopterin, 0.4–2.0 mM NADPH and 60 μM L-arginine containing 0.9 μCi of L-[2,3-3H]-arginine. For constitutive NOS, calmodulin was included at a final concentration of 40–100 nM. Following incubation at 37° C. for 15 minutes, the reaction was terminated by addition of 300 μL cold buffer containing 10 mM EGTA, 100 mM HEPES (pH5.5) and 1.0 mM L-citrulline. The [3H]-citrulline was separated by chromatography on Dowex 50W X-8 cation exchange resin and radioactivity quantified with a liquid scintillation counter.

1. Bredt, D. S. and Snyder, S. H. (1990) *Proc. Natl. Acad. Sci. U.S.A.* 87, 682–685.
2. Misko, T. P., Moore, W. M., Kasten, T. P., Nickols, G. A., Corbett, J. A., Tilton, R. G., McDaniel, M. L., Williamson, J. R. and Currie, M. G. (1993) *Eur. J. Pharm.* 233, 119–125.

Raw Cell Nitrite Assay

RAW 264.7 cells are plated to confluency on a 96-well tissue culture plate grown overnight (17 h) in the presence of LPS to induce NOS. A row of 3–6 wells are left untreated and served as controls for subtraction of nonspecific background. The media is removed from each well and the cells are washed twice with Krebs-Ringers-Hepes (25 mM, pH 7.4) with 2 mg/ml glucose. The cells are then placed on ice and incubated with 50 μL of buffer containing L-arginine (30 μM) +/–inhibitors for 1 h. The assay is initiated by warming the plate to 37° C. in a water bath for 1 h. Production of nitrite by intracellular iNOS is linear with time. To terminate the cellular assay, the plate of cells is placed on ice and the nitrite-containing buffer removed and analyzed for nitrite using a previously published fluorescent determination for nitrite. All values are the average of triplicate wells and are compared to a background-subtracted induced set of cells (100% value).

The following examples were assayed with the following results.

| Example number | hiNOS $IC_{50}$ (μM) | hecNOS $IC_{50}$ (μM) | hncNOS $IC_{50}$ (μM) | RAW cell i-NOS $IC_{50}$ | % inhibiton iNOS at 100 μM |
|---|---|---|---|---|---|
| 1 | 61 | 1990 | 898 | 300 | |
| 2 | | | | | * |
| 1d | | | | | 35 |
| 4 | | | | | 33 |
| 6 | | | | | 9 |
| 2d | | | | | 5 |
| 3B | 12.3 | 8420 | 150 | 80 | |
| 15A | 9.3 | 2350 | 99.6 | 57.3 | |
| 15B | 187 | 6590 | 441 | | |
| 16B | 76.8 | 5430 | 670 | >100 | |
| 3A | | | | | 53.4 |
| 48 | | | | | 40.6 |
| 40A | | | | | 32.6 |
| 41 | | | | | 28.5 |
| 49 | | | | | 19.4 |
| 40B | | | | | 14.5 |
| 11B | | | | | 4.6 |
| 10f | | | | | 7.7 |
| 10 | | | | | 3.4 |
| 11A | | | | | * |
| 12 | | | | | * |
| 18 | | | | | 7 |
| 19 | | | | | 54 |
| 5 | | | | | 27 |

-continued

| Example number | hiNOS IC$_{50}$ ($\mu$M) | hecNOS IC$_{50}$ ($\mu$M) | hncNOS IC$_{50}$ ($\mu$M) | RAW cell i-NOS IC$_{50}$ | % inhibiton iNOS at 100 $\mu$M |
|---|---|---|---|---|---|
| 50 |  |  |  |  | 40.6 |
| 14 |  |  |  |  | * |

*At 100 $\mu$M dose, response was not seen.

From the foregoing description, one skilled in the art can easily ascertain the essential characteristics of this invention, and without departing from the spirit and scope thereof, can make various changes and modifications of the invention to adapt it to various usages and conditions.

What is claimed:

1. A compound or a pharmaceutically acceptable salt, prodrug or ester thereof having the formula:

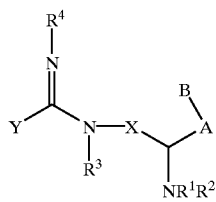

Y is hydrogen, lower alkyl radical, lower alkenyl radical, lower alkynyl radical, aromatic hydrocarbon radical, or alicyclic hydrocarbon radical, wherein all said radicals may optionally be substituted with hydrogen, lower alkyl, nitro, amino, alicyclic hydrocarbon radicals, or aromatic hydrocarbon radicals which may be optionally substituted with lower alkyl;

X is lower alkylene radical, lower alkenylene radical, lower alkynylene radical, aromatic hydrocarbon radical, $(CH_2)_mQ(CH_2)_n$, where m=1–3, n =1–3, and Q is sulfur, sulfinyl, sulfonyl, oxygen, carbonyl, lower alkynyl radical, aromatic hydrocarbon radical, or alicyclic hydrocarbon radical wherein all said radicals are optionally substituted with hydrogen, halogen and lower alkyl;

$R^1$, R $R^3$ and $R^4$ are independently selected from the group consisting of hydrogen and lower alkyl;

A is lower alkyl radical, lower alkenyl radical,lower alkynyl radical, alicyclic hydrocarbon radical, carbonyl, or aromatic hydrocarbon radical, wherein all said radicals are optionally substituted with hydrogen, lower alkyl, hydroxyl, lower alkoxy, alkoxycarbonyl, alkylaryloxy, thiol, lower thioalkoxy, thioalkylaryloxy, thioaryloxy, sulfinylalkyl, sulfinylalkylaryl, sulfinylaryl, sulfonylalkyl, sulfonylalkylaryl, sulfonylaryl, halogen, aromatic hydrocarbon radicals, or alicyclic hydrocarbon radicals;

B is hydrogen, lower alkyl radical, lower alkenyl radical, lower alkynyl radical, lower alkoxy radical, hydroxy, alkylaryloxy, thiol, lower thioalkoxy, lower thioalkylaryloxy, thioaryloxy, sulfinylalkyl, sulfinylalkylaryl, sulfinylaryl, sulfonylalkyl, sulfonylalkylaryl, sulfonylaryl, aromatic hydrocarbon radical, alicyclic hydrocarbon radical, or NHOH, wherein all said radicals are optionally substituted with hydrogen, lower alkyl, hydroxyl, lower alkoxy, halogen, aromatic hydrocarbon radicals,or alicyclic hydrocarbon radical;

with the proviso that when A is CHOR, B cannot be OR and Y cannot be amino wherein R is alkyl;

with the proviso that when A is carbonyl, B is not hydroxy, aryloxy, thioalkoxy, alkoxy, or NHOH.

2. The compound as recited in claim 1 wherein;

Y is hydrogen, lower alkyl radical, lower alkenyl radical, lower alkynyl radical, aromatic hydrocarbon radical, or alicyclic hydrocarbon radical, wherein all said radicals may optionally be substituted with hydrogen, cyano, lower alkyl, nitro, amino, alicyclic hydrocarbon radicals, or aromatic hydrocarbon radicals which may be optionally substituted with lower alkyl;

X is lower alkylene radical, lower alkenylene radical, lower alkynylene radical, aromatic hydrocarbon radical, $(CH_2)_mQ(CH_2)_n$, where m=1–3, n =1–3, and Q is sulfur, sulfinyl, sulfonyl, oxygen, carbonyl, lower alkynyl radical, aromatic hydrocarbon radical, or alicyclic hydrocarbon radical, wherein all said radicals are optionally substituted with hydrogen, halogen and lower alkyl;

$R^1$, R , $R^3$ and $R^4$ are independently selected from the group consisting of hydrogen and lower alkyl;

A is lower alkyl radical, lower alkenyl radical,lower alkynyl radical, alicyclic hydrocarbon radical, or aromatic hydrocarbon radical, wherein all said radicals are optionally substituted with hydrogen, lower alkyl, hydroxyl, lower alkoxy, alkylaryloxy, thiol, lower thioalkoxy, thioalkylaryloxy, thioaryloxy, sulfinylalkyl, sulfinylalkylaryl, sulfinylaryl, sulfonylalkyl, sulfonylalkylaryl, sulfonylaryl, halogen, aromatic hydrocarbon radicals, or alicyclic hydrocarbon radicals;

B is hydrogen, lower alkoxy radical, hydroxy, alkylaryloxy, thiol, lower thioalkoxy, lower thioalkylaryloxy, thioaryloxy, sulfinylalkyl, sulfinylalkylaryl, sulfinylaryl, sulfonylalkyl, sulfonylalkylaryl, sulfonylaryl, or NHOH.

3. A compound or a pharmaceutically acceptable salt, prodrug or ester thereof having the formula:

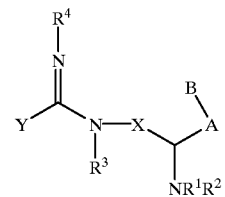

wherein;

Y is hydrogen or lower alkyl which may optionally be substituted with hydrogen, lower alkyl, nitro, amino, alicyclic hydrocarbon radicals, or aromatic hydrocarbon radicals which may be optionally substituted with lower alkyl;

X is lower alkylene from 3–5 carbons which may optionally be substituted with hydrogen, halogen and lower alkyl;

$R^1$, $R^2$, $R^3$ and $R^4$ are independently selected from the group consisting of hydrogen and lower alkyl;

A is lower alkylene from 2–4 carbons optionally substituted with hydroxyl B is hydroxyl.

4. The compound as recited in claim 3 wherein;

Y is methyl;

X is butylene;

$R^1$, $R^2$, $R^3$, and $R^4$ are hydrogen;

A is ethylene or isopropylene optionally substituted with hydroxyl and

B is hydroxyl.

5. The compound as recited in claim 1 wherein;

A is lower alkyl substituted with hydrogen, lower alkyl, hydroxyl, lower alkoxy, halogen, aromatic hydrocarbon radicals, or alicyclic hydrocarbon radicals.

6. The compound as recited in claim 1 wherein the compound is selected from the group consisting of;

N1-(1-iminoethyl)-1,4-pentanediamine;
N1-(1-iminoethyl)-1,5-heptanediamine;
N1-(1-iminoethyl)-5-phenyl-1,5-pentanediamine;
N-[5-amino-5-(2-hydroxyphenyl)pentyl]ethanimidamide;
N-[5-amino-5-(4-hydroxyphenyl)pentyl]ethanimidamide;
N-(5-aminononyl)ethanimidamide;
N-(5S-amino-6-oxoheptyl)ethanimidamide, dihydrochloride;
N-(5S-amino-6,7-dihydroxy-6-methylheptyl) ethanimidamide, hydrochloride dihydrate;
N-(5S-amino-6,7-dihydroxyoctyl)ethanimidamide, dihydrochloride hydrate;
N-(5S-amino-6,7,8-trihydroxyoctyl)ethanimidamide;
N-(5S-amino-7,8-dihydroxyoctyl)ethanimidamide;
N-(5S-amino-6-hydroxy-7-methoxyheptyl) ethanimidamide;
N-[5S-amino-6-hydroxy-7-(ethylthio)heptyl] ethanimidamide;
N-[5S-amino-6-hydroxy-7-methylsulfinyl)heptyl] ethanimidamide;
N-[5S-amino-6-hydroxy-7-methylsulfonyl)heptyl] ethanimidamide;
N-[5S-amino-6-hydroxy-7-(phenylmethyl)thio]heptyl] ethanimidamide;
N-[5S-amino-6-hydroxy-7-[(phenylmethyl) sulfinyl] heptyl]ethanimidamide;
N-[5S-amino-6-hydroxy-7-[(phenylmethyl)sulfonyl] heptyl]ethanimidamide;
N-(5S-amino-6-fluoro-7-hydroxy-6-methylheptyl) ethanimidamide;
N-[5S-amino-6-hydroxy-7-(2-hydroxyphenyl)heptyl] ethanimidamide, dihydrochloride;
N-[5S-amino-7,7,7-trifluoro-6-hydroxy-6-methylheptyl) ethanimidamide;
N-(5S-amino-6-hydroxyheptyl)ethanimidamide, dihydrochloride dihydrate;
N-[5S-amino-6-hydroxy-6-(2-hydroxyphenyl)hexyl] ethanimidamide;
N-(5S-amino-6-hydroxyhexyl)ethanimidamide; and
-[1-amino-5-[(1-iminoethyl)amino]pentyl] benzenemethanol hydrochloride dihydrate.

7. The compound as recited in claim 3 wherein the compound is N-(5S-amino-6,7-dihydroxyheptyl) ethanimidamide, dihydrochloride; and N-(5S-amino-6,7-dihydroxy-6-methylheptyl)ethanimidamide, hydrochloride dihydrate.

8. A pharmaceutical composition comprising a compound as recited in claim 1 together with a pharmaceutically acceptable carrier.

9. A pharmaceutical composition comprising a compound as recited in claim 2 together with a pharmaceutically acceptable carrier.

10. A pharmaceutical composition comprising a compound as recited in claim 3, 4, 5, 6, or 7 together with a pharmaceutically acceptable carrier.

11. A method of inhibiting nitric oxide synthesis in a subject in need of such inhibition by administering a therapeutically effective amount of a compound having the formula:

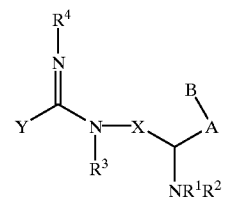

wherein:

Y is hydrogen, lower alkyl radical, lower alkenyl radical, lower alkynyl radical, aromatic hydrocarbon radical, or alicyclic hydrocarbon radical, wherein all said radicals may optionally be substituted with hydrogen, lower alkyl, nitro, amino, alicyclic hydrocarbon radicals, or aromatic hydrocarbon radicals which may be optionally substituted with lower alkyl;

X is lower alkylene radical, lower alkenylene radical, lower alkynylene radical, aromatic hydrocarbon radical, $(CH_2)_m Q(CH_2)_n$, where m=1–3, n=1–3, and Q is sulfur, sulfinyl, sulfonyl, oxygen, carbonyl, lower alkynyl radical, aromatic hydrocarbon radical, or alicyclic hydrocarbon radical wherein all said radicals are optionally substituted with hydrogen, halogen and lower alkyl;

$R^1$, $R^2$, $R^3$ and $R^4$ are independently selected from the group consisting of hydrogen and lower alkyl;

A is lower alkyl radical, lower alkenyl radical, lower alkynyl radical, alicyclic hydrocarbon radical, carbonyl, or aromatic hydrocarbon radical, wherein all said radicals are optionally substituted with hydrogen, lower alkyl, hydroxyl, lower alkoxy, alkoxycarbonyl, alkylaryloxy, thiol, lower thioalkoxy, thioalkylaryloxy, thioaryloxy, sulfinylalkyl, sulfinylalkylaryl, sulfinylaryl, sulfonylalkyl, sulfonylalkylaryl, sulfonylaryl, halogen, aromatic hydrocarbon radicals, or alicyclic hydrocarbon radicals;

B is hydrogen, lower alkyl radical, lower alkenyl radical, lower alkynyl radical, lower alkoxy radical, hydroxy, alkylaryloxy, thiol, lower thioalkoxy, lower thioalkylaryloxy, thioaryloxy, sulfinylalkyl, sulfinylalkylaryl, sulfinylaryl, sulfonylalkyl, sulfonylalkylaryl, sulfonylaryl, aromatic hydrocarbon radical, alicyclic hydrocarbon radical, or NHOH, wherein all said radicals are optionally substituted with hydrogen, lower alkyl, hydroxyl, lower alkoxy, halogen, aromatic hydrocarbon radicals,or alicyclic hydrocarbon radical;

with the proviso that when A is CHOR, B cannot be OR and Y cannot be amino wherein R is alkyl;

with the proviso that when A is carbonyl, B is not hydroxy, aryloxy, thioalkoxy, alkoxy, or NHOH.

12. The method of claim 11 wherein:

Y is hydrogen, lower alkyl radical, lower alkenyl radical, lower alkynyl radical, aromatic hydrocarbon radical, or alicyclic hydrocarbon radical, wherein all said radicals may optionally be substituted with hydrogen, cyano, lower alkyl, nitro, amino, alicyclic hydrocarbon radicals, or aromatic hydrocarbon radicals which may be optionally substituted with lower alkyl;

X is lower alkylene radical, lower alkenylene radical, lower alkynylene radical, aromatic hydrocarbon radical, $(CH_2)_mQ(CH_2)_n$, where m=1–3, n=1–3, and Q is sulfur, sulfinyl, sulfonyl, oxygen, carbonyl, lower alkynyl radical, aromatic hydrocarbon radical, or alicyclic hydrocarbon radical, wherein all said radicals are optionally substituted with hydrogen, halogen and lower alkyl;

$R^1$, $R^2$, $R^3$ and $R^4$ are independently selected from the group consisting of hydrogen and lower alkyl;

A is lower alkyl radical, lower alkenyl radical, lower alkynyl radical, alicyclic hydrocarbon radical, or aromatic hydrocarbon radical, wherein all said radicals are optionally substituted with hydrogen, lower alkyl, hydroxyl, lower alkoxy, alkylaryloxy, thiol, lower thioalkoxy, thioalkylaryloxy, thioaryloxy, sulfinylalkyl, sulfinylalkylaryl, sulfinylaryl, sulfonylalkyl, sulfonylalkylaryl, sulfonylaryl, halogen, aromatic hydrocarbon radicals, or alicyclic hydrocarbon radicals;

B is hydrogen, lower alkoxy radical, hydroxy, alkylaryloxy, thiol, lower thioalkoxy, lower thioalkylaryloxy, thioaryloxy, sulfinylalkyl, sulfinylalkylaryl, sulfinylaryl, sulfonylalkyl, sulfonylalkylaryl, sulfonylaryl, or NHOH.

13. A method of inhibiting nitric oxide synthesis in a subject in need of such inhibition by administering a therapeutically effective amount of a compound having the formula:

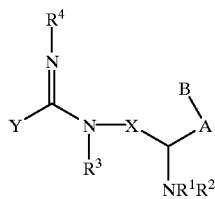

wherein:

Y is hydrogen or lower alkyl which may optionally be substituted with hydrogen, lower alkyl, nitro, amino, alicyclic hydrocarbon radicals, or aromatic hydrocarbon radicals which may be optionally substituted with lower alkyl;

X is lower alkylene from 3–5 carbons which may optionally substituted with hydrogen, halogen and lower alkyl;

$R^1$, $R^2$, $R^3$ and $R^4$ are independently selected from the group consisting of hydrogen and lower alkyl;

A is lower alkylene from 2–4 carbons optionally substituted with hydroxyl B is hydroxyl.

14. The method of claim 13 wherein:
Y is methyl;
X is butylene;
$R^1$, $R^2$, $R^3$, and $R^4$ are hydrogen;
A is ethylene or isopropylene optionally substituted with hydroxyl and
B is hydroxyl.

15. The method of claim 11 wherein:
A is lower alkyl substituted with hydrogen, lower alkyl, hydroxyl, lower alkoxy, halogen, aromatic hydrocarbon radicals, or alicyclic hydrocarbon radicals.

16. The method of claim 11 wherein the compound is selected from the group consisting of:
N1-(1-iminoethyl)-1,4-pentanediamine;
N1-(1-iminoethyl)-1,5-heptanediamine;
N1-(1-iminoethyl)-5-phenyl-1,5-pentanediamine;
N-[5-amino-5-(2-hydroxyphenyl)pentyl]ethanimidamide;
N-[5-amino-5-(4-hydroxyphenyl)pentyl]ethanimidamide;
N-(5-aminononyl)ethanimidamide;
N-(5S-amino-6-oxoheptyl)ethanimidamide, dihydrochloride;
N-(5S-amino-6,7-dihydroxy-6-methylheptyl) ethanimidamide, hydrochloride dihydrate;
N-(5S-amino-6,7-dihydroxyoctyl)ethanimidamide, dihydrochloride hydrate;
N-(5S-amino-6,7,8-trihydroxyoctyl)ethanimidamide;
N-(5S-amino-7,8-dihydroxyoctyl)ethanimidamide;
N-(5S-amino-6-hydroxy-7-methoxyheptyl) ethanimidamide;
N-[5S-amino-6-hydroxy-7-(ethylthio)heptyl] ethanimidamide;
N-[5S-amino-6-hydroxy-7-methylsulfinyl)heptyl] ethanimidamide;
N-[5S-amino-6-hydroxy-7-methylsulfonyl)heptyl] ethanimidamide;
N-[5S-amino-6-hydroxy-7-(phenylmethyl)thio]heptyl] ethanimidamide;
N-[5S-amino-6-hydroxy-7-[(phenylmethyl) sulfinyl] heptyl]ethanimidamide;
N-[5S-amino-6-hydroxy-7-[(phenylmethyl)sulfonyl] heptyl]ethanimidamide;
N-(5S-amino-6-fluoro-7-hydroxy-6-methylheptyl) ethanimidamide;
N-[5S-amino-6-hydroxy-7-(2-hydroxyphenyl)heptyl] ethanimidamide, dihydrochloride;
N-(5S-amino-7,7,7-trifluoro-6-hydroxy-6-methylheptyl) ethanimidamide;
N-(5S-amino-6-hydroxyheptyl)ethanimidamide, dihydrochloride dihydrate;
N-[5S-amino-6-hydroxy-6-(2-hydroxyphenyl)hexyl] ethanimidamide;
N-(5S-amino-6-hydroxyhexyl)ethanimidamide; and
-[1-amino-5-[(1-iminoethyl)amino]pentyl] benzenemethanol hydrochloride dihydrate.

17. A method of selectively inhibiting nitric oxide synthesis produced by inducible NO synthase over nitric oxide produced by the constitutive forms of NO synthase in a subject in need of such selective inhibition by administering a therapeutically effective amount of a compound having the formula:

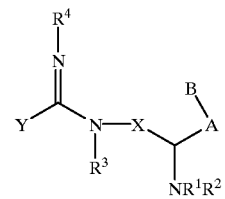

wherein:

Y is hydrogen, lower alkyl radical, lower alkenyl radical, lower alkynyl radical, aromatic hydrocarbon radical, or alicyclic hydrocarbon radical, wherein all said radicals may optionally be substituted with hydrogen, lower alkyl, nitro, amino, alicyclic hydrocarbon radicals, or aromatic hydrocarbon radicals which may be optionally substituted with lower alkyl;

X is lower alkylene radical, lower alkenylene radical, lower alkynylene radical, aromatic hydrocarbon radical, $(CH_2)_mQ(CH_2)_n$, where m=1–3, n=1–3, and Q is sulfur, sulfinyl, sulfonyl, oxygen, carbonyl, lower alkynyl radical, aromatic hydrocarbon radical, or alicyclic hydrocarbon radical wherein all said radicals are optionally substituted with hydrogen, halogen and lower alkyl;

$R^1$, $R^2$, $R^3$ and $R^4$ are independently selected from the group consisting of hydrogen and lower alkyl;

A is lower alkyl radical, lower alkenyl radical, lower alkynyl radical, alicyclic hydrocarbon radical, carbonyl, or aromatic hydrocarbon radical, wherein all said radicals are optionally substituted with hydrogen, lower alkyl, hydroxyl, lower alkoxy, alkoxycarbonyl, alkylaryloxy, thiol, lower thioalkoxy, thioalkylaryloxy, thioaryloxy, sulfinylalkyl, sulfinylalkylaryl, sulfinylaryl, sulfonylalkyl, sulfonylalkylaryl, sulfonylaryl, halogen, aromatic hydrocarbon radicals, or alicyclic hydrocarbon radicals;

B is hydrogen, lower alkyl radical, lower alkenyl radical, lower alkynyl radical, lower alkoxy radical, hydroxy, alkylaryloxy, thiol, lower thioalkoxy, lower thioalkylaryloxy, thioaryloxy, sulfinylalkyl, sulfinylalkylaryl, sulfinylaryl, sulfonylalkyl, sulfonylalkylaryl, sulfonylaryl, aromatic hydrocarbon radical, alicyclic hydrocarbon radical, or NHOH, wherein all said radicals are optionally substituted with hydrogen, lower alkyl, hydroxyl, lower alkoxy, halogen, aromatic hydrocarbon radicals, or alicyclic hydrocarbon radical;

with the proviso that when A is CHOR, B cannot be OR and Y cannot be amino wherein R is alkyl;

with the proviso that when A is carbonyl, B is not hydroxy, aryloxy, thioalkoxy, alkoxy, or NHOH.

18. The method of claim 17 wherein:

Y is hydrogen, lower alkyl radical, lower alkenyl radical, lower alkynyl radical, aromatic hydrocarbon radical, or alicyclic hydrocarbon radical, wherein all said radicals may optionally be substituted with hydrogen, cyano, lower alkyl, nitro, amino, alicyclic hydrocarbon radicals, or aromatic hydrocarbon radicals which may be optionally substituted with lower alkyl;

X is lower alkylene radical, lower alkenylene radical, lower alkynylene radical, aromatic hydrocarbon radical, $(CH_2)_mQ(CH_2)_n$, where m=1–3, n=1–3, and Q is sulfur, sulfinyl, sulfonyl, oxygen, carbonyl, lower alkynyl radical, aromatic hydrocarbon radical, or alicyclic hydrocarbon radical, wherein all said radicals are optionally substituted with hydrogen, halogen and lower alkyl;

$R^1$, $R^2$, $R^3$ and $R^4$ are independently selected from the group consisting of hydrogen and lower alkyl;

A is lower alkyl radical, lower alkenyl radical, lower alkynyl radical, alicyclic hydrocarbon radical, or aromatic hydrocarbon radical, wherein all said radicals are optionally substituted with hydrogen, lower alkyl, hydroxyl, lower alkoxy, alkylaryloxy, thiol, lower thioalkoxy, thioalkylaryloxy, thioaryloxy, sulfinylalkyl, sulfinylalkylaryl, sulfinylaryl, sulfonylalkyl, sulfonylalkylaryl, sulfonylaryl, halogen, aromatic hydrocarbon radicals, or alicyclic hydrocarbon radicals;

B is hydrogen, lower alkoxy radical, hydroxy, alkylaryloxy, thiol, lower thioalkoxy, lower thioalkylaryloxy, thioaryloxy, sulfinylalkyl, sulfinylalkylaryl, sulfinylaryl, sulfonylalkyl, sulfonylalkylaryl, sulfonylaryl, or NHOH.

19. A method of selectively inhibiting nitric oxide synthesis produced by inducible NO synthase over nitric oxide produced by the constitutive forms of NO synthase in a subject in need of such selective inhibition by administering a therapeutically effective amount of a compound having the formula:

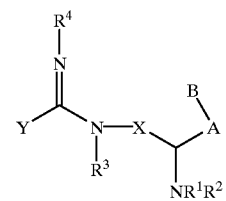

wherein:

Y is hydrogen or lower alkyl which may optionally be substituted with hydrogen, lower alkyl, nitro, amino, alicyclic hydrocarbon radicals, or aromatic hydrocarbon radicals which may be optionally substituted with lower alkyl;

X is lower alkylene from 3–5 carbons which may optionally substituted with hydrogen, halogen and lower alkyl;

$R^1$, $R^2$, $R^3$ and $R^4$ are independently selected from the group consisting of hydrogen and lower alkyl;

A is lower alkylene from 2–4 carbons optionally substituted with hydroxyl B is hydroxyl.

20. The method of claim 19 wherein:

Y is methyl;

X is butylene;

$R^1$, $R^2$, $R^3$, and $R^4$ are hydrogen;

A is ethylene or isopropylene optionally substituted with hydroxyl and

B is hydroxyl.

21. The method of claim 17 wherein:

A is lower alkyl substituted with hydrogen, lower alkyl, hydroxyl, lower alkoxy, halogen, aromatic hydrocarbon radicals, or alicyclic hydrocarbon radicals.

22. The method of claim 17 wherein the compound is selected from the group consisting of:

N1-(1-iminoethyl)-1,4-pentanediamine;

N1-(1-iminoethyl)-1,5-heptanediamine;

N1-(1-iminoethyl)-5-phenyl-1,5-pentanediamine;

N-[5-amino-5-(2-hydroxyphenyl)pentyl]ethanimidamide;

N-[5-amino-5-(4-hydroxyphenyl)pentyl]ethanimidamide;

N-(5-aminononyl)ethanimidamide;

N-(5S-amino-6-oxoheptyl)ethanimidamide, dihydrochloride;

N-(5S-amino-6,7-dihydroxy-6-methylheptyl) ethanimidamide, hydrochloride dihydrate;

N-(5S-amino-6,7-dihydroxyoctyl)ethanimidamide, dihydrochloride hydrate;

N-(5S-amino-6,7,8-trihydroxyoctyl)ethanimidamide;

N-(5S-amino-7,8-dihydroxyoctyl)ethanimidamide;

N-(5S-amino-6-hydroxy-7-methoxyheptyl) ethanimidamide;

N-[5S-amino-6-hydroxy-7-(ethylthio)heptyl] ethanimidamide;

N-[5S-amino-6-hydroxy-7-methylsulfinyl)heptyl] ethanimidamide;

N-[5S-amino-6-hydroxy-7-methylsulfonyl)heptyl] ethanimidamide;
N-[5S-amino-6-hydroxy-7-(phenylmethyl)thio]heptyl] ethanimidamide;
N-[5S-amino-6-hydroxy-7-[(phenylmethyl) sulfinyl] heptyl]ethanimidamide;
N-[5S-amino-6-hydroxy-7-[(phenylmethyl)sulfonyl] heptyl]ethanimidamide;
N-(5S-amino-6-fluoro-7-hydroxy-6-methylheptyl) ethanimidamide;
N-[5S-amino-6-hydroxy-7-(2-hydroxyphenyl)heptyl] ethanimidamide, dihydrochloride;
N-[5S-amino-7,7,7-trifluoro-6-hydroxy-6-methylheptyl) ethanimidamide;
N-(5S-amino-6-hydroxyheptyl)ethanimidamide, dihydrochloride dihydrate;
N-[5S -amino-6-hydroxy-6-(2-hydroxyphenyl)hexyl] ethanimidamide;
N-(5S-amino-6-hydroxyhexyl)ethanimidamide; and
-[1-amino-5-[(1-iminoethyl)amino]pentyl] benzenemethanol hydrochloride dihydrate.

23. A method of inhibiting nitric oxide synthesis in a subject in need of such inhibition by administering a therapeutically effective amount of a compound having the formula:

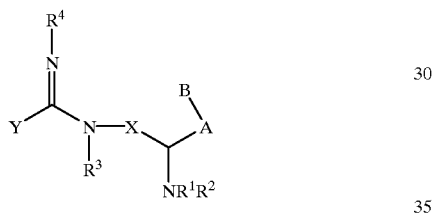

wherein:
Y is hydrogen, lower alkyl radical, lower alkenyl radical, lower alkynyl radical, aromatic hydrocarbon radical, or alicyclic hydrocarbon radical, wherein all said radicals may optionally be substituted with hydrogen, lower alkyl, nitro, amino, alicyclic hydrocarbon radicals, or aromatic hydrocarbon radicals which may be optionally substituted with lower alkyl;
X is lower alkylene radical, lower alkenylene radical, lower alkynylene radical, aromatic hydrocarbon radical, $(CH_2)_mQ(CH_2)_n$, where m=1–3, n=1–3, and Q is sulfur, sulfinyl, sulfonyl, oxygen, carbonyl, lower alkynyl radical, aromatic hydrocarbon radical, or alicyclic hydrocarbon radical wherein all said radicals are optionally substituted with hydrogen, halogen and lower alkyl;
$R^1$, $R^2$, $R^3$ and $R^4$ are independently selected from the group consisting of hydrogen and lower alkyl;
A is lower alkyl radical, lower alkenyl radical,lower alkynyl radical, alicyclic hydrocarbon radical, carbonyl, or aromatic hydrocarbon radical, wherein all said radicals are optionally substituted with hydrogen, lower alkyl, hydroxyl, lower alkoxy, alkoxycarbonyl, alkylaryloxy, thiol, lower thioalkoxy, thioalkylaryloxy, thioaryloxy, sulfinylalkyl, sulfinylalkylaryl, sulfinylaryl, sulfonylalkyl, sulfonylalkylaryl, sulfonylaryl, halogen, aromatic hydrocarbon radicals, or alicyclic hydrocarbon radicals;
B is hydrogen, lower alkyl radical, lower alkenyl radical, lower alkynyl radical, lower alkoxy radical, hydroxy, alkylaryloxy, thiol, lower thioalkoxy, lower thioalkylaryloxy, thioaryloxy, sulfinylalkyl, sulfinylalkylaryl, sulfinylaryl, sulfonylalkyl, sulfonylalkylaryl, sulfonylaryl, aromatic hydrocarbon radical, alicyclic hydrocarbon radical, or NHOH, wherein all said radicals are optionally substituted with hydrogen, lower alkyl, hydroxyl, lower alkoxy, halogen, aromatic hydrocarbon radicals,or alicyclic hydrocarbon radical;
with the proviso that when A is CHOR, B cannot be OR and Y cannot be amino wherein R is alkyl;
with the proviso that when A is carbonyl, B is not hydroxy, aryloxy, thioalkoxy, alkoxy, or NHOH.

24. The method of claim 23 wherein:
Y is hydrogen, lower alkyl radical, lower alkenyl radical, lower alkynyl radical, aromatic hydrocarbon radical, or alicyclic hydrocarbon radical, wherein all said radicals may optionally be substituted with hydrogen, cyano, lower alkyl, nitro, amino, alicyclic hydrocarbon radicals, or aromatic hydrocarbon radicals which may be optionally substituted with lower alkyl;
X is lower alkylene radical, lower alkenylene radical, lower alkynylene radical, aromatic hydrocarbon radical, $(CH_2)_mQ(CH_2)_n$, where m=1–3, n=1–3, and Q is sulfur, sulfinyl, sulfonyl, oxygen, carbonyl, lower alkynyl radical, aromatic hydrocarbon radical, or alicyclic hydrocarbon radical, wherein all said radicals are optionally substituted with hydrogen, halogen and lower alkyl;
$R^1$, $R^2$, $R^3$ and $R^4$ are independently selected from the group consisting of hydrogen and lower alkyl;
A is lower alkyl radical, lower alkenyl radical,lower alkynyl radical, alicyclic hydrocarbon radical, or aromatic hydrocarbon radical, wherein all said radicals are optionally substituted with hydrogen, lower alkyl, hydroxyl, lower alkoxy, alkylaryloxy, thiol, lower thioalkoxy, thioalkylaryloxy, thioaryloxy, sulfinylalkyl, sulfinylalkylaryl, sulfinylaryl, sulfonylalkyl, sulfonylalkylaryl, sulfonylaryl, halogen, aromatic hydrocarbon radicals, or alicyclic hydrocarbon radicals;
B is hydrogen, lower alkoxy radical, hydroxy, alkylaryloxy, thiol, lower thioalkoxy, lower thioalkylaryloxy, thioaryloxy, sulfinylalkyl, sulfinylalkylaryl, sulfinylaryl, sulfonylalkyl, sulfonylalkylaryl, sulfonylaryl, or NHOH.

25. A method of inhibiting nitric oxide synthesis in a subject in need of such inhibition by administering a therapeutically effective amount of a compound having the formula:

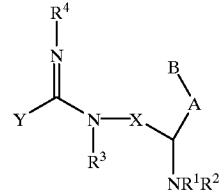

wherein:
Y is hydrogen or lower alkyl which may optionally be substituted with hydrogen, lower alkyl, nitro, amino, alicyclic hydrocarbon radicals, or aromatic hydrocarbon radicals which may be optionally substituted with lower alkyl;
X is lower alkylene from 3–5 carbons which may optionally substituted with hydrogen, halogen and lower alkyl;

$R^1$, $R^2$, $R^3$ and $R^4$ are independently selected from the group consisting of hydrogen and lower alkyl;

A is lower alkylene from 2–4 carbons optionally substituted with hydroxyl B is hydroxyl.

26. The method of claim 23 wherein:

Y is methyl;

X is butylene;

$R^1$, $R^2$, $R^3$, and $R^4$ are hydrogen;

A is ethylene or isopropylene optionally substituted with hydroxyl and

B is hydroxyl.

27. The method of claim 23 wherein:

A is lower alkyl substituted with hydrogen, lower alkyl, hydroxyl, lower alkoxy, halogen, aromatic hydrocarbon radicals, or alicyclic hydrocarbon radicals.

28. The method of claim 23 wherein the compound is selected from the group consisting of:

N1-(1-iminoethyl)-1,4-pentanediamine;

N1-(1-iminoethyl)-1,5-heptanediamine;

N1-(1-iminoethyl)-5-phenyl-1,5-pentanediamine;

N-[5-amino-5-(2-hydroxyphenyl)pentyl]ethanimidamide;

N-[5-amino-5-(4-hydroxyphenyl)pentyl]ethanimidamide;

N-(5-aminononyl)ethanimidamide;

N-(5S-amino-6-oxoheptyl)ethanimidamide, dihydrochloride;

N-(5S-amino-6,7-dihydroxy-6-methylheptyl) ethanimidamide, hydrochloride dihydrate;

N-(5S-amino-6,7-dihydroxyoctyl)ethanimidamide, dihydrochloride hydrate;

N-(5S-amino-6,7,8-trihydroxyoctyl)ethanimidamide;

N-(5S-amino-7,8-dihydroxyoctyl)ethanimidamide;

N-(5S-amino-6-hydroxy-7-methoxyheptyl) ethanimidamide;

N-[5S-amino-6-hydroxy-7-(ethylthio)heptyl] ethanimidamide;

N-[5S-amino-6-hydroxy-7-methylsulfinyl)heptyl] ethanimidamide;

N-[5S-amino-6-hydroxy-7-methylsulfonyl)heptyl] ethanimidamide;

N-[5S-amino-6-hydroxy-7-(phenylmethyl)thio]heptyl] ethanimidamide;

N-[5S-amino-6-hydroxy-7-[(phenylmethyl) sulfinyl] heptyl]ethanimidamide;

N-[5S-amino-6-hydroxy-7-[(phenylmethyl)sulfonyl] heptyl]ethanimidamide;

N-(5S-amino-6-fluoro-7-hydroxy-6-methylheptyl) ethanimidamide;

N-[5S-amino-6-hydroxy-7-(2-hydroxyphenyl)heptyl] ethanimidamide, dihydrochloride;

N-[5S-amino-7,7,7-trifluoro-6-hydroxy-6-methylheptyl] ethanimidamide;

N-(5S-amino-6-hydroxyheptyl)ethanimidamide, dihydrochloride dihydrate;

N-[5S-amino-6-hydroxy-6-(2-hydroxyphenyl)hexyl] ethanimidamide;

N-(5S-amino-6-hydroxyhexyl)ethanimidamide; and

-[1-amino-5-[(1-iminoethyl)amino]pentyl] benzenemethanol hydrochloride dihydrate.

* * * * *